(12) United States Patent
Gonzá#lez et al.

(10) Patent No.: US 9,844,552 B2
(45) Date of Patent: Dec. 19, 2017

(54) METHODS OF TREATING FIBROSIS

(71) Applicant: Pharmacyclics LLC, Sunnyvale, CA (US)

(72) Inventors: Toni Jauset Gonzá#lez, Lleida (ES); Daniel Massó-Vallés, Barcelona (ES); Laura Soucek, Barcelona (ES)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 14/957,294

(22) Filed: Dec. 2, 2015

(65) Prior Publication Data

US 2016/0199376 A1      Jul. 14, 2016

Related U.S. Application Data

(60) Provisional application No. 62/086,945, filed on Dec. 3, 2014.

(51) Int. Cl.
| | | |
|---|---|---|
| *A61K 31/519* | (2006.01) | |
| *C09B 31/147* | (2006.01) | |
| *A61K 31/7068* | (2006.01) | |

(52) U.S. Cl.
CPC ........ *A61K 31/519* (2013.01); *A61K 31/7068* (2013.01); *C09B 31/147* (2013.01)

(58) Field of Classification Search
CPC . A61K 31/519; A61K 31/7068; C09B 31/147
USPC ...................................... 514/262.1
See application file for complete search history.

(56) References Cited

U.S. PATENT DOCUMENTS

| | | |
|---|---|---|
| 7,514,444 B2 | 4/2009 | Honigberg et al. |
| 7,608,635 B2 | 10/2009 | Ying et al. |
| 7,732,454 B2 | 6/2010 | Verner |
| 7,825,118 B2 | 11/2010 | Honigberg et al. |
| 8,088,781 B2 | 1/2012 | Honigberg et al. |
| 8,883,803 B2 | 11/2014 | Honigberg et al. |
| 9,107,924 B2 | 8/2015 | Buggy et al. |
| 9,278,100 B2 | 3/2016 | Honigberg et al. |
| 9,415,050 B2 | 8/2016 | Chen et al. |
| 2008/0076921 A1 | 3/2008 | Honigberg et al. |
| 2008/0108636 A1 | 5/2008 | Honigberg et al. |
| 2008/0139582 A1 | 6/2008 | Honigberg et al. |
| 2009/0181987 A1 | 7/2009 | Honigberg et al. |
| 2011/0224235 A1 | 9/2011 | Honigberg et al. |
| 2013/0005746 A1 | 1/2013 | Honigberg et al. |
| 2013/0012525 A1 | 1/2013 | Honigberg et al. |
| 2014/0079690 A1 | 3/2014 | Buggy et al. |
| 2014/0336206 A1 | 11/2014 | Honigberg et al. |
| 2015/0044217 A1 | 2/2015 | Chen et al. |
| 2015/0118209 A1 | 4/2015 | Byrd et al. |
| 2015/0157634 A1 | 6/2015 | Blazar et al. |
| 2015/0158846 A1 | 6/2015 | Crawford et al. |
| 2016/0000792 A1 | 1/2016 | Buggy et al. |
| 2017/0151243 A1 | 6/2017 | Chen et al. |

FOREIGN PATENT DOCUMENTS

| | | |
|---|---|---|
| WO | WO-2008/039218 A2 | 4/2008 |
| WO | WO-2010/009342 A2 | 1/2010 |
| WO | WO-2015/023703 A1 | 2/2015 |
| WO | WO-2015/061751 A1 | 4/2015 |
| WO | WO-2015/084857 A1 | 6/2015 |
| WO | WO-2015/149056 A1 | 10/2015 |

OTHER PUBLICATIONS

International Search Report and Written Opinion for PCT/US15/63475 dated Mar 28, 2016.
Mahadevan, D et al. Tumor-stroma interactions in pancreatic ductal adenocarcinoma. Molecular Cancer Therapy, vol. 6, No. 4, Apr. 2007, pp. 1186-1197, p. 1192.
Philip, PA et al. Phase II Study of Gemcitabine and Cisplatin in the Treatment of Patients with Advanced Pancreatic Carcinoma . CANCER, vol. 92, No. 3, Aug. 1, 2001, pp. 569-577.
Sherman, MH et al. Vitamin D Receptor-Mediated Stromal Reprogramming Suppresses pancreatitis and Enhances Pancreatic Cancer Therapy. Cell, vol. 159, Sep. 25, 2014, pp. 80-93.
Volinia, S., et al., A microRNA expression signature of human solid tumors defines cancer gene targets, Proceedings of the National Academy of Sciences of the United States of America, vol. 13, No. 7, Feb. 14, 2006, pp. 2257-2261; p. 2257-2258.
Dubovsky, J. A., et al., "Ibrutinib Treatment Ameliorates Murine Chronic Graft-Versus-Host Disease," Journal of Clinical Investigation, vol. 124 (11), 10 pages. (Nov. 2014) DOI: 10.1172/JCI75328.
Taiwan Search Report for Application No. 104140382, dated Aug. 25, 2016, 1 page.

*Primary Examiner* — Kristin Vajda
(74) *Attorney, Agent, or Firm* — Foley Hoag LLP

(57) ABSTRACT

Disclosed are methods of treating fibrosis in a patient, comprising administering to a patient in need thereof a therapeutically effective amount of an ACK inhibitor (e.g., a BTK inhibitor, such as for example an irreversible BTK inhibitor, such as for example, ibrutinib).

6 Claims, 5 Drawing Sheets

Vehicle　　　　　Ibrutinib

Vehicle　　　　　Ibrutinib

SEQUENCE LISTING

```
<160> NUMBER OF SEQ ID NOS: 1

<210> SEQ ID NO 1
<211> LENGTH: 15
<212> TYPE: PRT
<213> ORGANISM: Unknown
<220> FEATURE:
<223> OTHER INFORMATION: Description of Unknown:
      peptide substrate for Bruton's tyrosine kinase

<400> SEQUENCE: 1

Ala Val Leu Glu Ser Glu Glu Glu Leu Tyr Ser Ser Ala Arg Gln
1               5                   10                  15
```

METHODS OF TREATING FIBROSIS

SUMMARY OF THE INVENTION

Disclosed herein, in some embodiments, are methods of treating fibrosis in a patient, comprising administering to a patient in need thereof a therapeutically effective amount of an ACK inhibitor (e.g., a BTK inhibitor, such as for example an irreversible BTK inhibitor, such as for example, ibrutinib). Disclosed herein, in some embodiments, are methods of treating fibrosis in a patient, comprising administering to a patient in need thereof a therapeutically effective amount of a compound of Formula (A) having the structure:

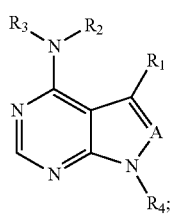

Formula (A)

wherein:
A is N;
$R_1$ is phenyl-O-phenyl or phenyl-S-phenyl;
$R_2$ and $R_3$ are independently H;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;
G is

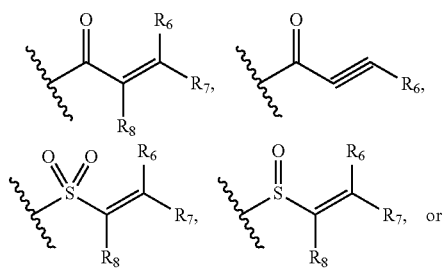

-continued

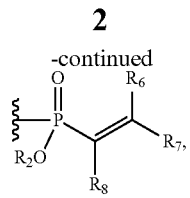

wherein,
$R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_{10}$ and $R_{11}$ can together form a 5-, 6-, 7-, or 8-membered heterocyclic ring; or
each $R_{11}$ is independently selected from H or substituted or unsubstituted alkyl; or a pharmaceutically acceptable salt thereof, thereby treating the fibrosis. In some embodiments, $L_3$, X and $L_4$ taken together form a nitrogen containing heterocyclic ring. In some embodiments, the nitrogen containing heterocyclic ring is a piperidine group. In some embodiments, the G is

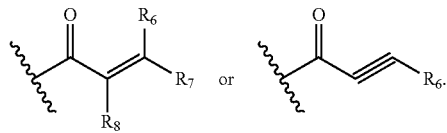

In some embodiments, the compound of Formula (A) is (R)-1-(3-(4-amino-3-(4-phenoxyphenyl)-1H-pyrazolo[3,4-d]pyrimidin-1-yl)piperidin-1-yl)prop-2-en-1-one (ibrutinib)

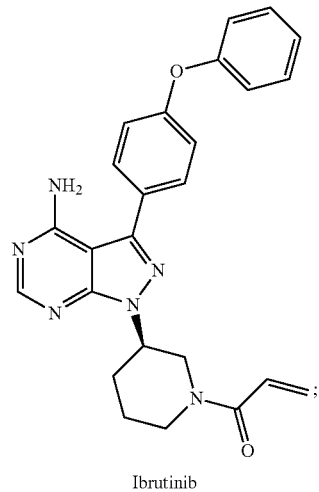

Ibrutinib or a pharmaceutically acceptable salt thereof. In some embodiments, the fibrosis is not associated with graft versus host disease (GVHD). In some embodiments, the fibrosis is not associated with sclerodermatous GVHD, lung chronic GVHD, or liver chronic GVHD. In some embodiments, the fibrosis is of the liver, lung, pancreas, kidney, bone marrow, heart, skin, intestine, or joints. In some embodiments, the fibrosis is of the lung. In some embodiments, the fibrosis is of the liver. In some embodiments, the fibrosis is of the pancreas. In some embodiments, the patient has cirrhosis, chronic pancreatitis, cystic fibrosis, or cancer. In some embodiments, the cancer is a solid tumor cancer. In some embodiments, the solid tumor cancer is selected from the group consisting of anal cancer; appendix cancer; bile duct cancer; bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; pancreatic ductal adenocarcinoma; parathyroid disease; penile cancer; pituitary tumor; prostate cancer; rectal cancer; skin cancer; stomach cancer; testicular cancer; throat cancer; thyroid cancer; uterine cancer; vaginal cancer; and vulvar cancer. In some embodiments, the solid tumor cancer is pancreatic cancer. In some embodiments the cancer is pancreatic ductal adenocarcinoma.

Disclosed herein, in some embodiments, are methods of pancreatic cancer in a patient, comprising administering to a patient in need thereof a therapeutically effective amount of an ACK inhibitor (e.g., a BTK inhibitor, such as for example an irreversible BTK inhibitor, such as for example ibrutinib) and a therapeutically effective amount of gemcitabine. Disclosed herein, in some embodiments, are methods of treating pancreatic cancer in a patient, comprising administering to a patient in need thereof a therapeutically effective amount of a compound of Formula (A) having the structure:

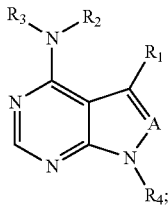

Formula (A)

wherein:
A is N;
$R_1$ is phenyl-O-phenyl or phenyl-S-phenyl;
$R_2$ and $R_3$ are independently H;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

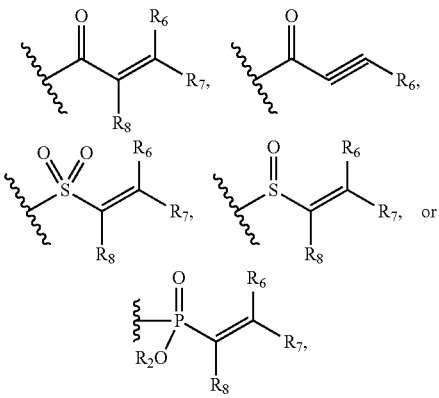

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof, and a therapeutic amount of gemcitabine, thereby treating the pancreatic cancer. In some embodiments, $L_3$, X and $L_4$ taken together form a nitrogen containing heterocyclic ring. In some embodiments, the nitrogen containing heterocyclic ring is a piperidine group. In some embodiments, G is

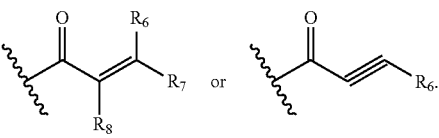

In some embodiments, the compound of Formula (A) is (R)-1-(3-(4-amino-3-(4-phenoxyphenyl)-1H-pyrazolo[3,4-d]pyrimidin-1-yl)piperidin-1-yl)prop-2-en-1-one (ibrutinib)

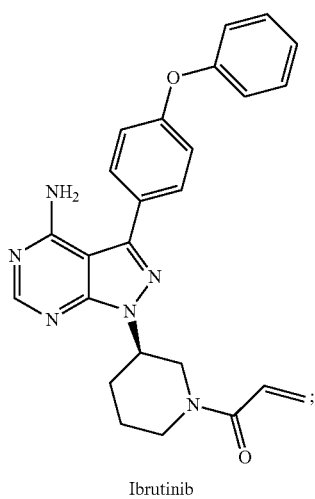 [SMILES: C=CC(=O)N1CCC[C@@H](n2nc(-c3ccc(Oc4ccccc4)cc3)c3c(N)ncnc32)C1]

Ibrutinib or a pharmaceutically acceptable salt thereof. In some embodiments, the pancreatic cancer is pancreatic ductal adenocarcinoma. In some embodiments, survival of the patient is increased as compared to administration of gemcitabine alone. In some embodiments, in pancreatic fibrosis is reduced. In some embodiments, co-administration of the ACK inhibitor (such as a compound of Formula A or ibrutinib) and gemcitabine is 5%, 10%, 15%, 20%, 25%, 30%, 35%, 40%, 45%, 50%, 55% or 60% more efficacious than administration of the gemcitabine alone. In some embodiments, co-administration of the ACK inhibitor and gemcitabine is 50% more efficacious than administration of gemcitabine alone. In some embodiments, co-administration of the ACK inhibitor and gemcitabine is 5%, 10%, 15%, 20%, 25%, 30%, or 35% more efficacious than administration of the ACK inhibitor alone. In some embodiments, co-administration of the ACK inhibitor and gemcitabine is 25% more efficacious than administration of the ACK inhibitor alone. In some embodiments, the ACK inhibitor and gemcitabine are administered in a unified dosage form or separate dosage forms. In some embodiments, the ACK inhibitor and gemcitabine are administered simultaneously or sequentially.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows histological analysis of 8 week old p53$^{ER/ER}$; LSLKRas$^{G12D}$; pdx1-Cre mice treated with ibrutinib (n=4) or vehicle control (n=4) for 4 weeks. Histological analysis of pancreata shows a reduction in Ki67 positive (proliferating) cells in ibrutinib-treated mice (14.9%, 95% CI=7.5% to 22.3%) compared to control animals (67.8%, 95% CI=36.9% to 98.7%), p value=0.0016. Three animals per condition and 5 sections per animal were analyzed for IHC quantification. FIG. 1B shows immunohistochemistry for CD11b (a leukocytic marker associated to monocytes, neutrophils, natural killer cells, granulocytes and macrophages) with clear reduction of CD11b positivity in ibrutinib-treated compared to vehicle-treated mice. FIG. 1C shows percentages of CD11b+ cells (CD45+CD11c−) and tumor-associated macrophages (CD45+CD11b+Ly6C-Ly6G-F4/80+) in single cell suspensions of normal pancreas isolated from negative untreated littermates [(−)LM], and from tumor bearing mice treated with ibrutinib or untreated, as assessed by flow cytometry and expressed as a percent of total cells. Results shown represent mean and error bars represent 95% confidence intervals. Statistical significance was determined via unpaired t-test with *p<0.05, p<0.01, *p<0.001. At least three animals per condition were analyzed. FIG. 1D shows Picrosirius Red Staining of pancreatic samples from negative littermates [(−)LM] and from tumor-bearing mice, treated with ibrutinib or vehicle. Animals treated with ibrutinib show a reduced amount of collagen compared to vehicle-treated animals. At least three animals per condition and 5 sections per animal were analyzed.

FIG. 2A shows histological analysis of 8 week old p53$^{ER/ER}$; LSLKRas$^{G12D}$; pdx1-Cre mice treated with intraperitoneal sodium cromoglycate (n=3) or vehicle control (n=3) for 4 weeks. Histological analysis of pancreata by Picrosirius Red Staining shows reduced collagen deposition in cromolyn-treated mice compared to vehicle-treated control animals. Three animals per condition and 5 sections per animal were analyzed. Staining shows collagen in the tumor stroma. FIG. 2B shows a reduction of collagen deposition in subcutaneous xenografts of a patient derived tumor in NOD/SCID mice during ibrutinib treatment. Picrosirius Red Staining was performed on tumor samples from untreated (n=6) or ibrutinib-treated mice (n=6) and indicates collagen deposition in the tumor stroma. Six animals per condition and 4 sections per animal were analyzed.

FIG. 3A shows treatment of p53$^{ER/ER}$; LSLKRas$^{G12D}$; pdx1-Cre mice with ibrutinib (n=11) or vehicle control (n=11) starting from 8 weeks of age. Ibrutinib alone confers survival advantage to the treated animals (p value=0.015). Log-rank test was utilized for statistical analysis of the data. FIG. 3B shows treatment of p53$^{ER/ER}$; LSLKRas$^{G12D}$; pdx1-Cre mice with gemcitabine (n=8) or with a combination of gemcitabine and ibrutinib (n=9), starting from 8 weeks of age. Addition of ibrutinib to standard of care improves animal survival (p value=0.026). Log-rank test was utilized for statistical analysis of the data.

DETAILED DESCRIPTION OF THE INVENTION

Figure 1A:
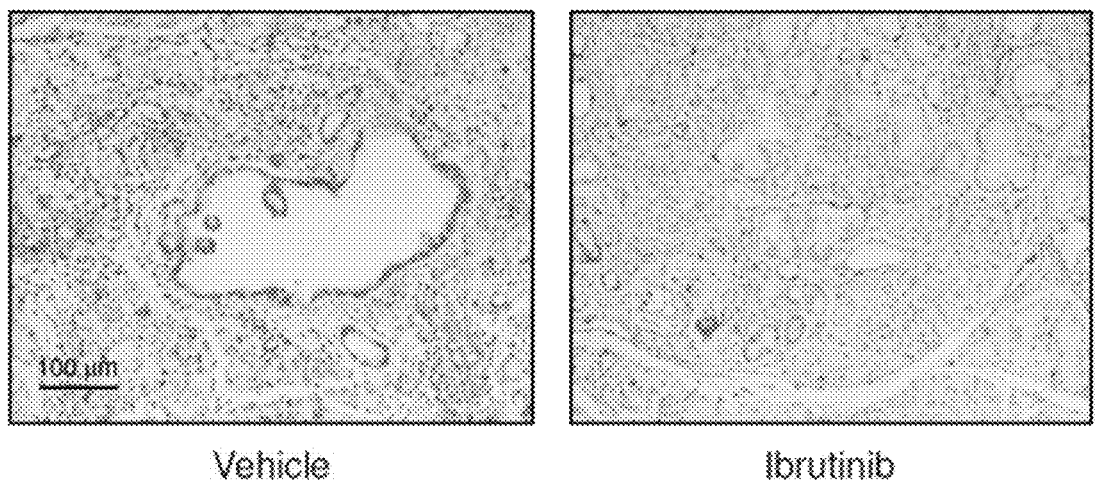
FIG. 1A-FIG. 1D illustrate the effect of ibrutinib treatment on the tumor microenvironment.

Disclosed herein, in some embodiments, are methods of treating fibrosis in a patient, comprising administering to a patient in need thereof a therapeutically effective amount of an ACK inhibitor (e.g., a BTK inhibitor, such as for example an irreversible BTK inhibitor, such as for example, ibrutinib). Disclosed herein, in some embodiments, are methods of treating fibrosis in a patient, comprising administering to a patient in need thereof a therapeutically effective amount of a compound of Formula (A) having the structure:

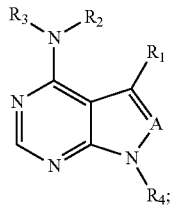

Formula (A)

wherein:
A is N;
$R_1$ is phenyl-O-phenyl or phenyl-S-phenyl;
$R_2$ and $R_3$ are independently H;
$R_4$ is $L_3$-X-$L_4$-G, wherein,
$L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;
X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;
$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;
or $L_3$, X and $L_4$ taken together form a nitrogen containing heterocyclic ring;
G is

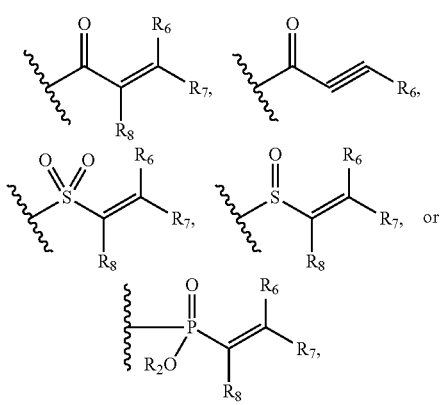

wherein,
$R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;
each $R_9$ is independently selected from among H, substituted or unsubstituted lower alkyl, and substituted or unsubstituted lower cycloalkyl;
each $R_{10}$ is independently H, substituted or unsubstituted lower alkyl, or substituted or unsubstituted lower cycloalkyl; or
two $R_{10}$ groups can together form a 5-, 6-, 7-, or 8-membered heterocyclic ring; or
$R_{10}$ and $R_{11}$ can together form a 5-, 6-, 7-, or 8-membered heterocyclic ring; or
each $R_{11}$ is independently selected from H or substituted or unsubstituted alkyl; or a pharmaceutically acceptable salt thereof, thereby treating the fibrosis. In some embodiments, $L_3$, X and $L_4$ taken together form a nitrogen containing heterocyclic ring. In some embodiments, the nitrogen containing heterocyclic ring is a piperidine group. In some embodiments, the G is

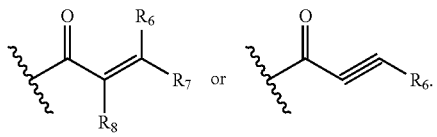

In some embodiments, the compound of Formula (A) is (R)-1-(3-(4-amino-3-(4-phenoxyphenyl)-1H-pyrazolo[3,4-d]pyrimidin-1-yl)piperidin-1-yl)prop-2-en-1-one (ibrutinib)

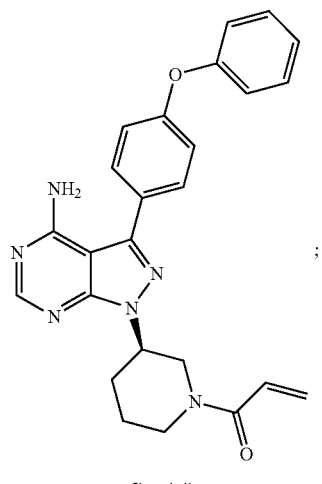

Ibrutinib or a pharmaceutically acceptable salt thereof. In some embodiments, the fibrosis is not associated with graft versus host disease (GVHD). In some embodiments, the fibrosis is not associated with sclerodermatous GVHD, lung chronic GVHD, or liver chronic GVHD. In some embodiments, the fibrosis is of the liver, lung, pancreas, kidney, bone marrow, heart, skin, intestine, or joints. In some embodiments, the fibrosis is of the liver. In some embodiments, the fibrosis is of the lung. In some embodiments, the fibrosis is of the pancreas. In some embodiments, the patient has cirrhosis, chronic pancreatitis, cystic fibrosis, or cancer. In some embodiments, the cancer is a solid tumor cancer. In some embodiments, the solid tumor cancer is selected from the group consisting of anal cancer; appendix cancer; bile duct cancer; bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; pancreatic ductal adenocarcinoma; parathyroid disease; penile cancer; pituitary tumor; prostate cancer; rectal cancer; skin cancer; stomach cancer; testicular cancer; throat cancer; thyroid cancer; uterine cancer; vaginal cancer; and vulvar cancer. In some embodiments, the solid tumor cancer is pancreatic cancer. In some embodiments the cancer is pancreatic ductal adenocarcinoma.

Disclosed herein, in some embodiments, are methods of pancreatic cancer in a patient, comprising administering to a patient in need thereof a therapeutically effective amount of an ACK inhibitor (e.g., a BTK inhibitor, such as for example an irreversible BTK inhibitor, such as for example ibrutinib) and a therapeutically effective amount of gemcitabine. Disclosed herein, in some embodiments, are methods of treating pancreatic cancer in a patient, comprising administering to a patient in need thereof a therapeutically effective amount of a compound of Formula (A) having the structure:

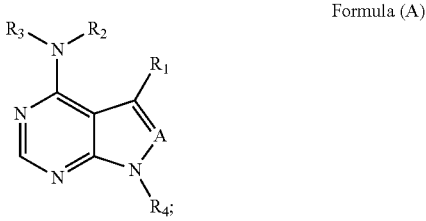

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

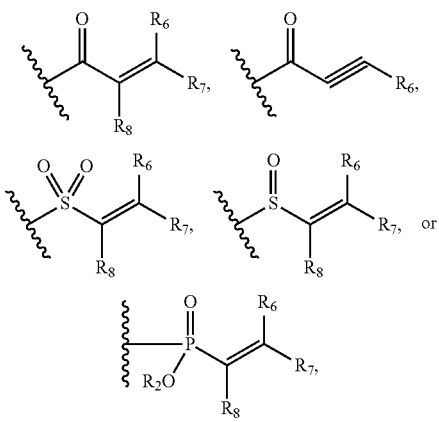

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof, and a therapeutic amount of gemcitabine, thereby treating the pancreatic cancer. In some embodiments, $L_3$, X and $L_4$ taken together form a nitrogen containing heterocyclic ring. In some embodiments, the nitrogen containing heterocyclic ring is a piperidine group. In some embodiments, G is

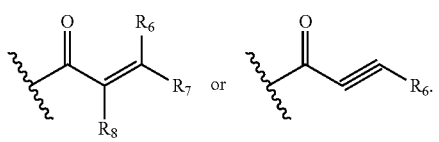

In some embodiments, the compound of Formula (A) is (R)-1-(3-(4-amino-3-(4-phenoxyphenyl)-1H-pyrazolo[3,4-d]pyrimidin-1-yl)piperidin-1-yl)prop-2-en-1-one (ibrutinib)

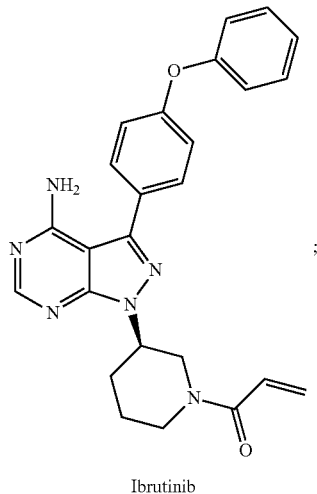 [SMILES: C=CC(=O)N1CCC[C@@H](n2nc(-c3ccc(Oc4ccccc4)cc3)c3c(N)ncnc32)C1]

Ibrutinib or a pharmaceutically acceptable salt thereof. In some embodiments, the pancreatic cancer is pancreatic ductal adenocarcinoma. In some embodiments, survival of the patient is increased as compared to administration of gemcitabine alone. In some embodiments, in pancreatic fibrosis is reduced. In some embodiments, co-administration of the ACK inhibitor (such as a compound of Formula A or ibrutinib) and gemcitabine is 5%, 10%, 15%, 20%, 25%, 30%, 35%, 40%, 45%, 50%, 55% or 60% more efficacious than administration of the gemcitabine alone. In some embodiments, co-administration of the ACK inhibitor and gemcitabine is 50% more efficacious than administration of gemcitabine alone. In some embodiments, co-administration of the ACK inhibitor and gemcitabine is 5%, 10%, 15%, 20%, 25%, 30%, or 35% more efficacious than administration of the ACK inhibitor alone. In some embodiments, co-administration of the ACK inhibitor and gemcitabine is 25% more efficacious than administration of the ACK inhibitor alone. In some embodiments, the ACK inhibitor and gemcitabine are administered in a unified dosage form or separate dosage forms. In some embodiments, the ACK inhibitor and gemcitabine are administered simultaneously or sequentially.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, "amelioration" refers to any lessening of severity, delay in onset, slowing of progression, or shortening of duration of tissue fibrosis, whether permanent or temporary, lasting or transient that can be attributed to or associated with administration of the compound or composition.

As used herein, "ACK" and "Accessible Cysteine Kinase" are synonyms. They mean a kinase with an accessible cysteine residue. ACKs include, but are not limited to, BTK, ITK, Bmx/ETK, TEC, EFGR, HER4, HER4, LCK, BLK, C-src, FGR, Fyn, HCK, Lyn, YES, ABL, Brk, CSK, FER, JAK3, SYK. In some embodiments, the ACK is a TEC family kinase. In some embodiments, the ACK is HER4. In some embodiments, the ACK is BTK. In some embodiments, the ACK is ITK.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g., a peptide substrate having the amino acid sequence "AVLESEEEL-YSSARQ" SEQ ID NO: 1).

The term "homologous cysteine," as used herein refers to a cysteine residue found within a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

The term "irreversible BTK inhibitor," as used herein, refers to an inhibitor of BTK that can form a covalent bond with an amino acid residue of BTK. In one embodiment, the irreversible inhibitor of BTK can form a covalent bond with a Cys residue of BTK; in particular embodiments, the irreversible inhibitor can form a covalent bond with a Cys 481 residue (or a homolog thereof) of BTK or a cysteine residue in the homologous corresponding position of another tyrosine kinase.

The terms "individual", "patient" and "subject" are used interchangeably. They refer to a mammal (e.g., a human), which is the object of treatment, or observation. The term is not to be construed as requiring the supervision of a medical practitioner (e.g., a physician, physician's assistant, nurse, orderly, hospice care worker).

The terms "treat," "treating" or "treatment", as used herein, include lessening of severity of tissue fibrosis, delay in onset of tissue fibrosis, causing regression of tissue fibrosis, relieving a condition caused by of tissue fibrosis, or stopping symptoms which result from tissue fibrosis. In the context of treatment of cancer, the terms include lessening of severity of a solid tumor, delay in onset of a solid tumor, slowing the growth of a solid tumor, slowing metastasis of cells of a solid tumor, shortening of duration of a solid tumor, arresting the development of o a solid tumor, causing regression of a solid tumor, relieving a condition caused by of a solid tumor, or stopping symptoms which result from a solid tumor. The terms "treat," "treating" or "treatment", include, but are not limited to, prophylactic and/or therapeutic treatments.

Fibrosis

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia. Examples of tissue fibrosis include, but are not limited to, pulmonary fibrosis, renal fibrosis, cardiac fibrosis, cirrhosis and fibrosis of the liver, skin scars and keloids, adhesions, fibromatosis, atherosclerosis, and amyloidosis.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is primary fibrosis. In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, the fibrotic condition is a fibrotic condition of the lung, a fibrotic condition of the liver, a fibrotic condition of the heart or vasculature, a fibrotic condition of the kidney, a fibrotic condition of the skin, a fibrotic condition of the gastrointestinal tract, a fibrotic condition of the bone marrow or a hematopoietic tissue, a fibrotic condition of the nervous system, or a combination thereof.

In some embodiments, the fibrotic condition affects a tissue chosen from one or more of muscle, tendon, cartilage, skin (e.g., skin epidermis or endodermis), cardiac tissue, vascular tissue (e.g., artery, vein), pancreatic tissue, lung tissue, liver tissue, kidney tissue, uterine tissue, ovarian tissue, neural tissue, testicular tissue, peritoneal tissue, colon, small intestine, biliary tract, gut, bone marrow, or hematopoietic tissue.

In some embodiments, the fibrotic condition is a fibrotic condition of the lung. In some embodiments, the fibrotic condition of the lung is chosen from one or more of: pulmonary fibrosis, idiopathic pulmonary fibrosis (IPF), usual interstitial pneumonitis (UIP), interstitial lung disease, cryptogenic fibrosing alveolitis (CFA), bronchiolitis obliterans, or bronchiectasis. In some embodiments, the fibrosis of the lung is secondary to a disease, a toxin, an insult, a medical treatment, or a combination thereof. In some embodiments, fibrosis of the lung is associated with one or more of: a disease process such as asbestosis and silicosis; an occupational hazard; an environmental pollutant; cigarette smoking; an autoimmune connective tissue disorders (e.g., rheumatoid arthritis, scleroderma and systemic lupus erythematosus (SLE)); a connective tissue disorder such as sarcoidosis; an infectious disease, e.g., infection, particularly chronic infection; a medical treatment, including but not limited to, radiation therapy, and drug therapy, e.g., chemotherapy (e.g., treatment with as bleomycin, methotrexate, amiodarone, busulfan, and/or nitrofurantoin). In some embodiments, the fibrotic condition of the lung treated with the methods of the invention is associated with (e.g., secondary to) a cancer treatment, e.g., treatment of a cancer (e.g. squamous cell carcinoma, testicular cancer, Hodgkin's disease with bleomycin).

In some embodiments, the fibrotic condition is a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

In some embodiments, the fibrotic condition is a fibrotic condition of the heart. In certain embodiments, the fibrotic condition of the heart is myocardial fibrosis (e.g., myocardial fibrosis associated with radiation myocarditis, a surgical procedure complication (e.g., myocardial post-operative fibrosis), infectious diseases (e.g., Chagas disease, bacterial, trichinosis or fungal myocarditis)); granulomatous, metabolic storage disorders (e.g., cardiomyopathy, hemochromatosis); developmental disorders (e.g., endocardial fibroelastosis); arteriosclerotic, or exposure to toxins or irritants (e.g., drug induced cardiomyopathy, drug induced cardiotoxicity, alcoholic cardiomyopathy, cobalt poisoning or exposure). In some embodiments, the myocardial fibrosis is associated with an inflammatory disorder of cardiac tissue (e.g., myocardial sarcoidosis).

In some embodiments, the fibrotic condition is a fibrotic condition of the kidney. In some embodiments, the fibrotic condition of the kidney is chosen from one or more of: renal fibrosis (e.g., chronic kidney fibrosis), nephropathies associated with injury/fibrosis (e.g., chronic nephropathies associated with diabetes (e.g., diabetic nephropathy)), lupus, scleroderma of the kidney, glomerular nephritis, focal segmental glomerular sclerosis, IgA nephropathyrenal fibrosis associated with human chronic kidney disease (CKD), chronic progressive nephropathy (CPN), tubulointerstitial fibrosis, ureteral obstruction, chronic uremia, chronic interstitial nephritis, radiation nephropathy, glomerulosclerosis, progressive glomerulonephrosis (PGN), endothelial/thrombotic microangiopathy injury, HIV-associated nephropathy, or fibrosis associated with exposure to a toxin, an irritant, or a chemotherapeutic agent.

In some embodiments, the fibrotic condition is a fibrotic condition of the skin. In some embodiments, the fibrotic condition of the skin is chosen from one or more of: skin fibrosis, scleroderma, nephrogenic systemic fibrosis (e.g., resulting after exposure to gadolinium which is frequently used as a contrast substance for MRIs in patients with severe kidney failure), scarring and keloid.

In some embodiments, the fibrotic condition is a fibrotic condition of the gastrointestinal tract. In some embodiments, the fibrotic condition is chosen from one or more of fibrosis associated with scleroderma; radiation induced gut fibrosis; fibrosis associated with a foregut inflammatory disorder such as Barrett's esophagus and chronic gastritis, and/or fibrosis associated with a hindgut inflammatory disorder, such as inflammatory bowel disease (IBD), ulcerative colitis and Crohn's disease.

In some embodiments, the fibrotic condition is adhesions. In some embodiments, the adhesions are chosen from one or more of: abdominal adhesions, peritoneal adhesions, pelvic adhesions, pericardial adhesions, peridural adhesions, peritendinous or adhesive capsulitis.

In some embodiments, the fibrotic condition is a fibrotic condition of the eye. In some embodiments, the fibrotic condition of the eye involves diseases of the anterior segment of the eye such as glaucoma and corneal opacification; in some embodiments, the fibrotic condition of the eye involves disease of the posterior segment of the eye such as age-related macular degeneration, diabetic retinopathy, retinopathy of prematurity and neovascular glaucoma; in some embodiments, the fibrotic condition of the eye results from fibrosis following ocular surgery.

In some embodiments, the fibrotic condition is a fibrotic condition of the bone marrow or a hematopoietic tissue. In some embodiments, the fibrotic condition of the bone marrow is an intrinsic feature of a chronic myeloproliferative neoplasm of the bone marrow, such as primary myelofibrosis (also referred to herein as agnogenic myeloid metaplasia or chronic idiopathic myelofibrosis). In some embodiments, the bone marrow fibrosis is associated with (e.g., is secondary to) a malignant condition or a condition caused by a clonal proliferative disease. In some embodiments, the bone marrow fibrosis is associated with a hematologic disorder (e.g., a hematologic disorder chosen from one or more of polycythemia vera, essential thrombocythemia, myelodysplasia, hairy cell leukemia, lymphoma (e.g., Hodgkin or non-Hodgkin lymphoma), multiple myeloma or chronic myelogeneous leukemia (CML)). In some embodiments, the bone marrow fibrosis is associated with (e.g., secondary to) a non-hematologic disorder (e.g., a non-hematologic disorder chosen from solid tumor metastasis to bone marrow, an autoimmune disorder (e.g., systemic lupus erythematosus, scleroderma, mixed connective tissue disorder, or polymyositis), an infection (e.g., tuberculosis), or secondary hyperparathyroidism associated with vitamin D deficiency.

In some embodiments, the fibrosis is not associated with graft versus host disease (GVHD). In some embodiments, the fibrosis is not associated with sclerodermatous GVHD, lung chronic GVHD, or liver chronic GVHD. In some embodiments, the fibrosis is of the liver, lung, pancreas, kidney, bone marrow, heart, skin, intestine, or joints. In some embodiments, the fibrosis is of the liver. In some embodiments, the fibrosis is of the lung. In some embodiments, the fibrosis is of the pancreas. In some embodiments, the patient has cirrhosis, chronic pancreatitis, cystic fibrosis, or cancer. In some embodiments, the cancer is a solid tumor cancer.

As used herein, a "solid tumor" is an abnormal mass of tissue resulting from the abnormal growth or division of cells (i.e., neoplasia). Solid tumors are characterized by an absence of liquid areas. In some embodiments, the solid tumor is benign. In some embodiments, the solid tumor is malignant (i.e., a cancer).

In some embodiments, the solid tumor is a sarcoma or carcinoma. In some embodiments, the solid tumor is a sarcoma. Sarcomas are cancers of the bone, cartilage, fat, muscle, blood vessels, or other connective or supportive tissue. In some embodiments, the sarcoma is selected from alveolar rhabdomyosarcoma; alveolar soft part sarcoma; ameloblastoma; angiosarcoma; chondrosarcoma; chordoma; clear cell sarcoma of soft tissue; dedifferentiated liposarcoma; desmoid; desmoplastic small round cell tumor; embryonal rhabdomyosarcoma; epithelioid fibrosarcoma; epithelioid hemangioendothelioma; epithelioid sarcoma; esthesioneuroblastoma; Ewing sarcoma; extrarenal rhabdoid tumor; extraskeletal myxoid chondrosarcoma; extraskeletal osteosarcoma; fibrosarcoma; giant cell tumor; hemangiopericytoma; infantile fibrosarcoma; inflammatory myofibroblastic tumor; Kaposi sarcoma; leiomyosarcoma of bone; liposarcoma; liposarcoma of bone; malignant fibrous histiocytoma (MFH); malignant fibrous histiocytoma (MFH) of bone; malignant mesenchymoma; malignant peripheral nerve sheath tumor; mesenchymal chondrosarcoma; myxofibrosarcoma; myxoid liposarcoma; myxoinflammatory fibroblastic sarcoma; neoplasms with perivascular epitheioid cell differentiation; osteosarcoma; parosteal osteosarcoma; neoplasm with perivascular epitheioid cell differentiation; periosteal osteosarcoma; pleomorphic liposarcoma; pleomorphic rhabdomyosarcoma; PNET/extraskeletal Ewing tumor; rhabdomyosarcoma; round cell liposarcoma; small cell osteosarcoma; solitary fibrous tumor; synovial sarcoma; telangiectatic osteosarcoma.

In some embodiments, the solid tumor is a carcinoma. Carcinomas are cancers that begin in the epithelial cells. Carcinomas are classified as adenocarcinoma, squamous cell carcinoma, adenosquamous carcinoma, anaplastic carcinoma, large cell carcinoma, small cell carcinoma. In some embodiments, the carcinoma is selected from an adenocarcinoma, squamous cell carcinoma, adenosquamous carcinoma, anaplastic carcinoma, large cell carcinoma, or small cell carcinoma. In some embodiments, the carcinoma is selected from anal cancer; appendix cancer; bile duct cancer (i.e., cholangiocarcinoma); bladder cancer; brain tumor; breast cancer; cervical cancer; colon cancer; cancer of Unknown Primary (CUP); esophageal cancer; eye cancer; fallopian tube cancer; kidney cancer; liver cancer; lung cancer; medulloblastoma; melanoma; oral cancer; ovarian cancer; pancreatic cancer; parathyroid disease; penile cancer; pituitary tumor; prostate cancer; rectal cancer; skin cancer; stomach cancer; testicular cancer; throat cancer; thyroid cancer; uterine cancer; vaginal cancer; or vulvar cancer. In some embodiments, the carcinoma is breast cancer. In some embodiments, the breast cancer is invasive ductal carcinoma, ductal carcinoma in situ, invasive lobular carcinoma, or lobular carcinoma in situ. In some embodiments, the carcinoma is pancreatic cancer. In some embodiments, the pancreatic cancer is adenocarcinoma, or islet cell carcinoma. In some embodiments, the carcinoma is colorectal cancer. In some embodiments, the colorectal cancer is adenocarcinoma. In some embodiments, the solid tumor is a colon polyp. In some embodiments, the colon polyp is associated with familial adenomatous polyposis. In some embodiments, the carcinoma is bladder cancer. In some embodiments, the bladder cancer is transitional cell bladder cancer, squamous cell bladder cancer, or adenocarcinoma. In some embodiments, the carcinoma is lung cancer. In some embodiments, the lung cancer is a non-small cell lung cancer. In some embodiments, the non-small cell lung cancer is adenocarcinoma, squamous-cell lung carcinoma, or large-cell lung carcinoma. In some embodiments, the lung cancer is a small cell lung cancer. In some embodiments, the carcinoma is prostate cancer. In some embodiments, the prostate cancer is adenocarcinoma or small cell carcinoma. In some embodiments, the carcinoma is ovarian cancer. In some embodiments, the ovarian cancer is epithelial ovarian cancer. In some embodiments, the carcinoma is bile duct cancer. In some embodiments, the bile duct cancer is proximal bile duct carcinoma or distal bile duct carcinoma.

Disclosed herein, in some embodiments, are methods of pancreatic cancer in a patient, comprising administering to a patient in need thereof a therapeutically effective amount of an ACK inhibitor (e.g., a BTK inhibitor, such as for example an irreversible BTK inhibitor, such as for example ibrutinib) and a therapeutically effective amount of gemcitabine. Pancreatic adenocarcinoma is characterized by dense desmoplasia, composed of extracellular matrix, endothelial cells, immune cells, fibroblasts and stellate cells. This epithelial and stromal compartment appears to enhance the aggressive nature of the disease and its resistance to therapy. Indeed, the dense stromal fibroinflammatory reaction results in decreased blood supply, poor drug delivery, and hypoxia.

ACK Inhibitor Compounds

Disclosed herein, in some embodiments, are methods of treating fibrosis in a patient, comprising administering to a patient in need thereof a therapeutically effective amount of an ACK inhibitor (e.g., a BTK inhibitor, such as for example an irreversible BTK inhibitor, such as for example, ibrutinib).

Disclosed herein, in some embodiments, are methods of pancreatic cancer in a patient, comprising administering to a patient in need thereof a therapeutically effective amount of an ACK inhibitor (e.g., a BTK inhibitor, such as for example an irreversible BTK inhibitor, such as for example ibrutinib) and a therapeutically effective amount of gemcitabine.

The ACK inhibitor compounds described herein are selective for kinases having an accessible cysteine that is able to form a covalent bond with a Michael acceptor moiety on the inhibitor compound. In some embodiments, the cysteine residue is accessible or becomes accessible when the binding site moiety of the irreversible inhibitor binds to the kinase. That is, the binding site moiety of the irreversible inhibitor binds to an active site of the ACK and the Michael acceptor moiety of irreversible inhibitor gains access (in one embodiment the step of binding leads to a conformational change in the ACK, thus exposing the cysteine) or is otherwise exposed to the cysteine residue of the ACK; as a result a covalent bond is formed between the "S" of the cysteine residue and the Michael acceptor of the irreversible inhibitor. Consequently, the binding site moiety of the irreversible inhibitor remains bound or otherwise blocks the active site of the ACK.

In some embodiments, the ACK is BTK, a homolog of BTK or a tyrosine kinase having a cysteine residue in an amino acid sequence position that is homologous to the amino acid sequence position of cysteine 481 in BTK. In some embodiments, the ACK is ITK. In some embodiments, the ACK is HER4. Inhibitor compounds described herein include a Michael acceptor moiety, a binding site moiety and a linker that links the binding site moiety and the Michael acceptor moiety (and in some embodiments, the structure of the linker provides a conformation, or otherwise directs the Michael acceptor moiety, so as to improve the selectivity of the irreversible inhibitor for a particular ACK). In some embodiments, the ACK inhibitor inhibits ITK and BTK.

In some embodiments, the ACK inhibitor is a compound of Formula (A):

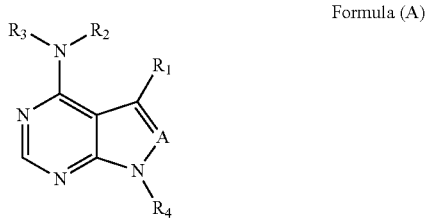

Formula (A)

wherein

A is independently selected from N or $CR_5$;

$R_1$ is H, $L_2$-(substituted or unsubstituted alkyl), $L_2$-(substituted or unsubstituted cycloalkyl), $L_2$-(substituted or unsubstituted alkenyl), $L_2$-(substituted or unsubstituted cycloalkenyl), $L_2$-(substituted or unsubstituted heterocycle), $L_2$-(substituted or unsubstituted heteroaryl), or $L_2$-(substituted or unsubstituted aryl), where $L_2$ is a bond, O, S, —S(=O), —S(=O)$_2$, C(=O), -(substituted or unsubstituted $C_1$-$C_6$ alkyl), or -(substituted or unsubstituted $C_2$-$C_6$ alkenyl);

$R_2$ and $R_3$ are independently selected from H, lower alkyl and substituted lower alkyl;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, O, —C(=O), S, —S(=O), —S(=O)$_2$, —NH, —NR$_9$, —NHC(O), —C(O)NH, —NR$_9$C(O), —C(O)NR$_9$, —S(=O)$_2$NH, —NHS(=O)$_2$, —S(=O)$_2$NR$_9$—, —NR$_9$S(=O)$_2$, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl, aryl, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

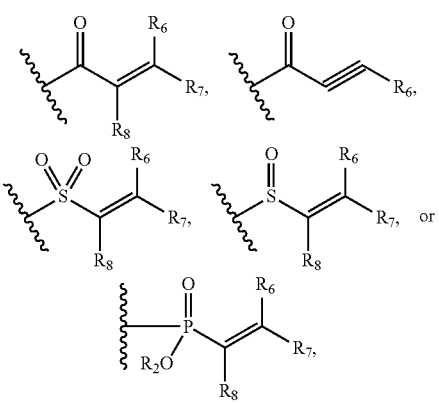

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_5$ is H, halogen, -$L_6$-(substituted or unsubstituted $C_1$-$C_3$ alkyl), -$L_6$-(substituted or unsubstituted $C_2$-$C_4$ alkenyl), -$L_6$-(substituted or unsubstituted heteroaryl), or -$L_6$-(substituted or unsubstituted aryl), wherein $L_6$ is a bond, O, S, —S(═O), S(═O)₂, NH, C(O), —NHC(O)O, —OC(O)NH, —NHC(O), or —C(O)NH;

each R₉ is independently selected from among H, substituted or unsubstituted lower alkyl, and substituted or unsubstituted lower cycloalkyl;

each R₁₀ is independently H, substituted or unsubstituted lower alkyl, or substituted or unsubstituted lower cycloalkyl; or two R₁₀ groups can together form a 5-, 6-, 7-, or 8-membered heterocyclic ring; or R₁₀ and R₁₁ can together form a 5-, 6-, 7-, or 8-membered heterocyclic ring; or each R₁₁ is independently selected from H or alkyl; and pharmaceutically active metabolites, pharmaceutically acceptable solvates, pharmaceutically acceptable salts, or pharmaceutically acceptable prodrugs thereof.

In some embodiments, the compound of Formula (A) is a BTK inhibitor. In some embodiments, the compound of Formula (A) is an ITK inhibitor. In some embodiments, the compound of Formula (A) inhibits ITK and BTK.

In some embodiments, the ACK inhibitor is (R)-1-(3-(4-amino-3-(4-phenoxyphenyl)-1H-pyrazolo[3,4-d]pyrimidin-1-yl)piperidin-1-yl)prop-2-en-1-one (i.e. PCI-32765/ibrutinib)

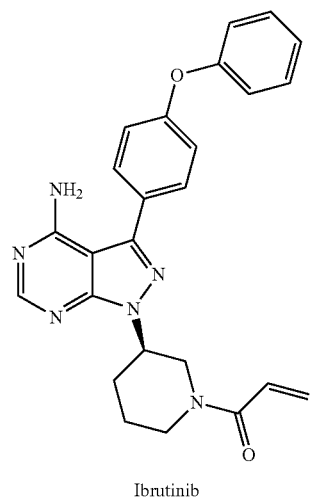

Ibrutinib

In some embodiments, the ACK inhibitor is ibrutinib, PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK4I7891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP-7536 (KBP BioSciences), ACP-196 (Acerta Pharma) or JTE-051 (Japan Tobacco Inc).

In some embodiments, the ACK inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3,3-dimethylbutan-2-ylamino)methyl]benzamide (BMS-509744, HY-11092); or N-(5-((5-(4-Acetylpiperazine-1-carbonyl)-4-methoxy-2-methylphenyl)thio)thiazol-2-yl)-4-(((3-methylbutan-2-yl)amino)methyl)benzamide (HY11066).

In some embodiments, the ACK inhibitor is:

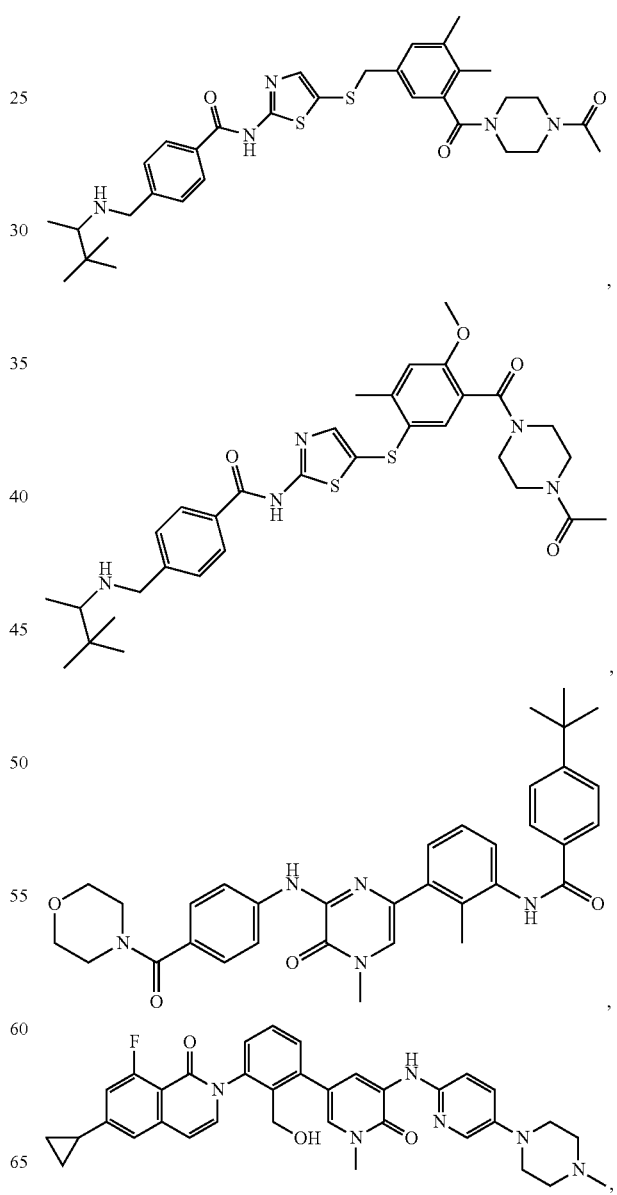

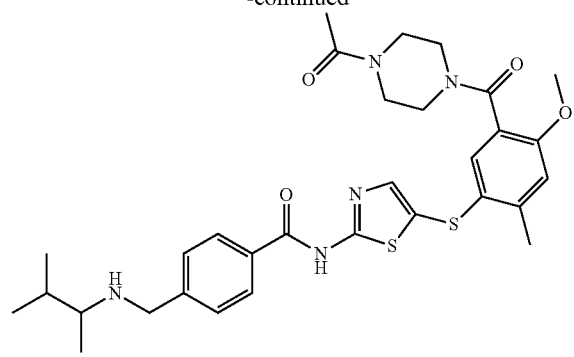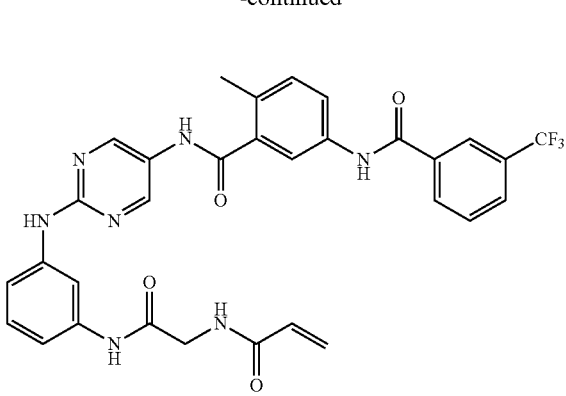

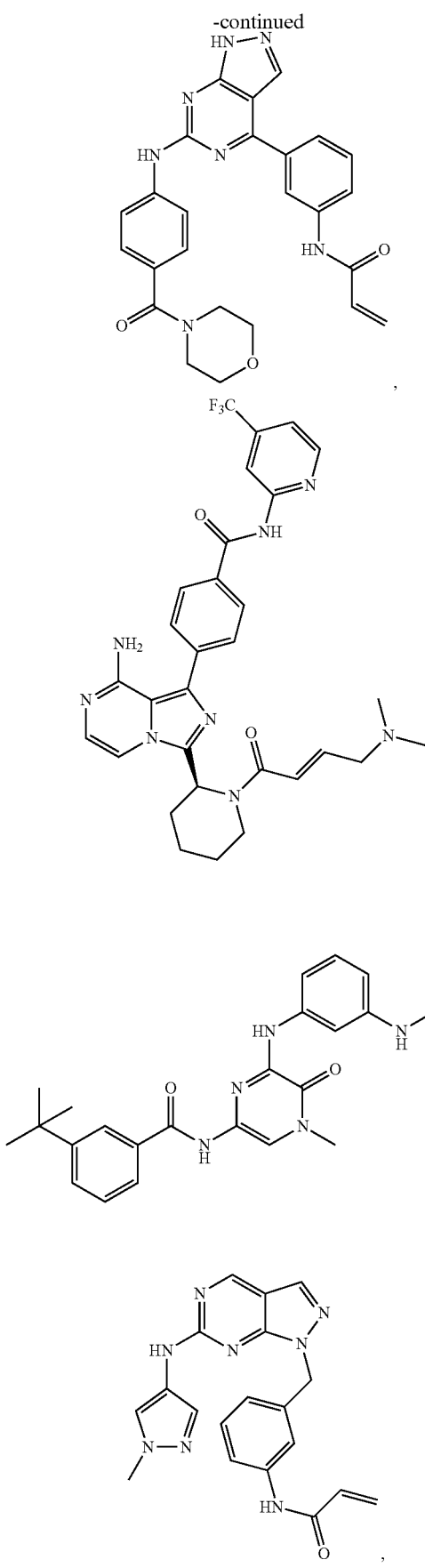
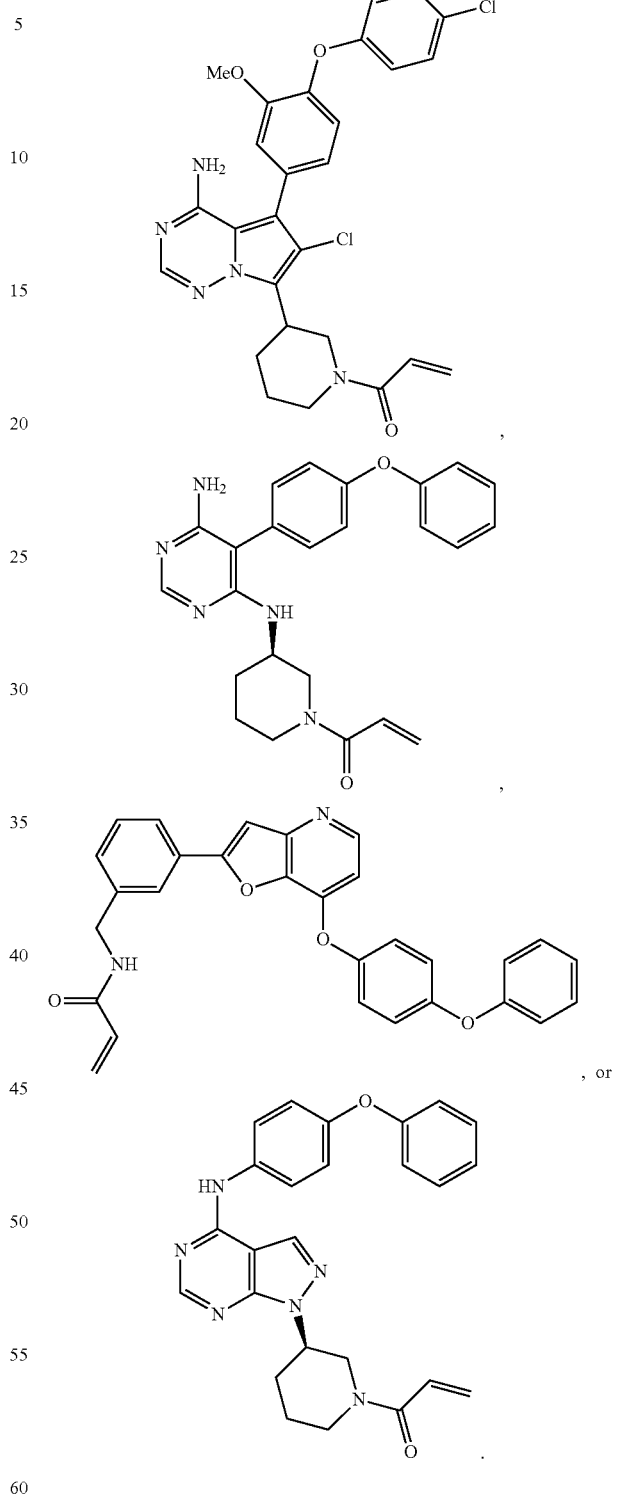
BTK Inhibitors
In some embodiments, the ACK inhibitor is a BTK inhibitor. The BTK inhibitor compounds described herein are selective for BTK and kinases having a cysteine residue in an amino acid sequence position of the tyrosine kinase that is homologous to the amino acid sequence position of cysteine 481 in BTK. The BTK inhibitor compound can form a covalent bond with Cys 481 of BTK (e.g., via a Michael reaction).

In some embodiments, the BTK inhibitor is a compound of Formula (A) having the structure:

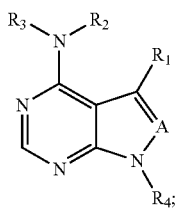

Formula (A)

wherein:

A is N;

$R_1$ is phenyl-O-phenyl or phenyl-S-phenyl;

$R_2$ and $R_3$ are independently H;

$R_4$ is $L_3$-X-$L_4$-G, wherein, $L_3$ is optional, and when present is a bond, optionally substituted or unsubstituted alkyl, optionally substituted or unsubstituted cycloalkyl, optionally substituted or unsubstituted alkenyl, optionally substituted or unsubstituted alkynyl;

X is optional, and when present is a bond, —O—, —C(=O)—, —S—, —S(=O)—, —S(=O)$_2$—, —NH—, —NR$_9$—, —NHC(O)—, —C(O)NH—, —NR$_9$C(O)—, —C(O)NR$_9$—, —S(=O)$_2$NH—, —NHS(=O)$_2$—, —S(=O)$_2$NR$_9$—, —NR$_9$S(=O)$_2$—, —OC(O)NH—, —NHC(O)O—, —OC(O)NR$_9$—, —NR$_9$C(O)O—, —CH=NO—, —ON=CH—, —NR$_{10}$C(O)NR$_{10}$—, heteroaryl-, aryl-, —NR$_{10}$C(=NR$_{11}$)NR$_{10}$—, —NR$_{10}$C(=NR$_{11}$)—, —C(=NR$_{11}$)NR$_{10}$—, —OC(=NR$_{11}$)—, or —C(=NR$_{11}$)O—;

$L_4$ is optional, and when present is a bond, substituted or unsubstituted alkyl, substituted or unsubstituted cycloalkyl, substituted or unsubstituted alkenyl, substituted or unsubstituted alkynyl, substituted or unsubstituted aryl, substituted or unsubstituted heteroaryl, substituted or unsubstituted heterocycle;

or $L_3$, X and $L_4$ taken together form a nitrogen containing heterocyclic ring;

G is

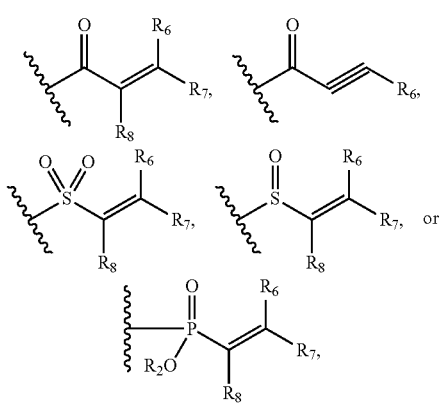

wherein, $R_6$, $R_7$ and $R_8$ are independently selected from among H, halogen, CN, OH, substituted or unsubstituted alkyl or substituted or unsubstituted heteroalkyl or substituted or unsubstituted cycloalkyl, substituted or unsubstituted heterocycloalkyl, substituted or unsubstituted aryl, substituted or unsubstituted heteroaryl;

each $R_9$ is independently selected from among H, substituted or unsubstituted lower alkyl, and substituted or unsubstituted lower cycloalkyl;

each $R_{10}$ is independently H, substituted or unsubstituted lower alkyl, or substituted or unsubstituted lower cycloalkyl; or two $R_{10}$ groups can together form a 5-, 6-, 7-, or 8-membered heterocyclic ring; or $R_{10}$ and $R_{11}$ can together form a 5-, 6-, 7-, or 8-membered heterocyclic ring; or each $R_{11}$ is independently selected from H or substituted or unsubstituted alkyl; or a pharmaceutically acceptable salt thereof. In some embodiments, $L_3$, X and $L_4$ taken together form a nitrogen containing heterocyclic ring. In some embodiments, the nitrogen containing heterocyclic ring is a piperidine group. In some embodiments, G is

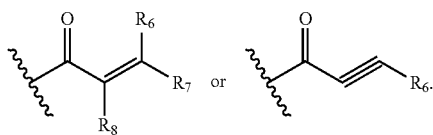

In some embodiments, the compound of Formula (A) is 1-[(3R)-3-[4-amino-3-(4-phenoxyphenyl)pyrazolo[3,4-d]pyrimidin-1-yl]piperidin-1-yl]prop-2-en-1-one.

In some embodiments, the BTK inhibitor compound of Formula (A) has the following structure of Formula (B):

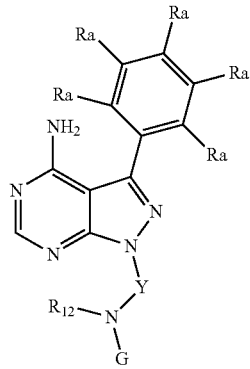

Formula (B)

wherein:

Y is alkyl or substituted alkyl, or a 4-, 5-, or 6-membered cycloalkyl ring;

each $R_a$ is independently H, halogen, —CF$_3$, —CN, —NO$_2$, OH, NH$_2$, -L$_a$-(substituted or unsubstituted alkyl), -L$_a$-(substituted or unsubstituted alkenyl), -L$_a$-(substituted or unsubstituted heteroaryl), or -L$_a$-(substituted or unsubstituted aryl), wherein L$_a$ is a bond, O, S, —S(=O), —S(=O)$_2$, NH, C(O), CH$_2$, —NHC(O)O, —NHC(O), or —C(O)NH;

G is

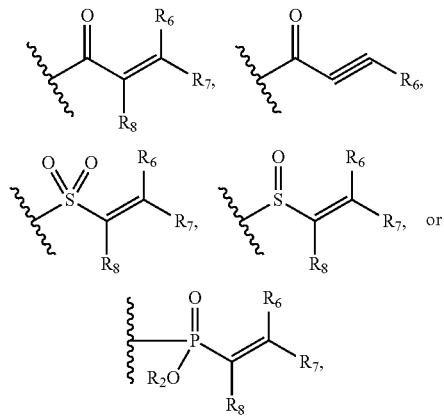

wherein, $R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl;

$R_{12}$ is H or lower alkyl; or

Y and $R_{12}$ taken together form a 4-, 5-, or 6-membered heterocyclic ring; and pharmaceutically acceptable active metabolites, pharmaceutically acceptable solvates, pharmaceutically acceptable salts, or pharmaceutically acceptable prodrugs thereof.

In some embodiments, G is selected from among

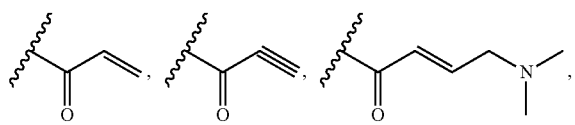

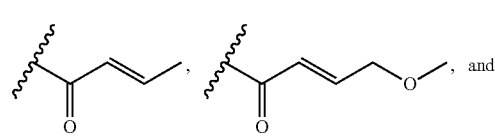

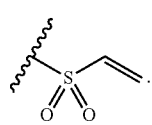

In some embodiments,

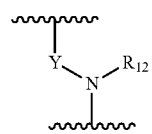

is selected from among

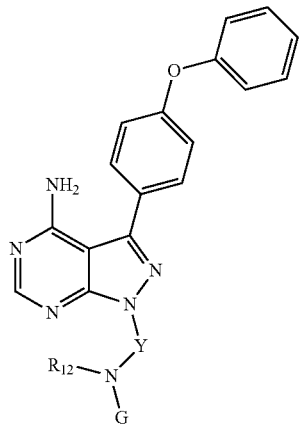

In some embodiments, the BTK inhibitor compound of Formula (B) has the following structure of Formula (C):

Formula (C)

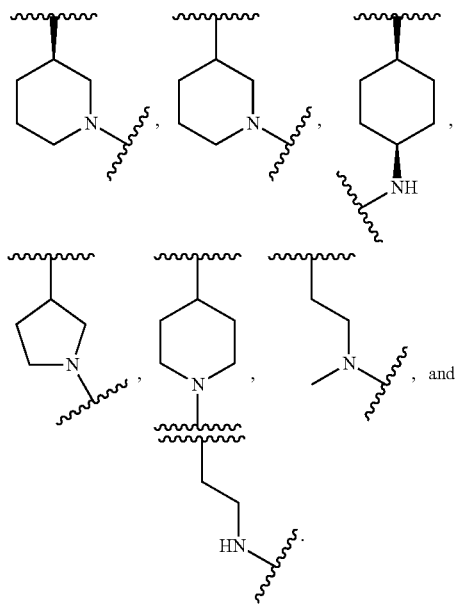

Y is alkyl or substituted alkyl, or a 4-, 5-, or 6-membered cycloalkyl ring;

$R_{12}$ is H or lower alkyl; or

Y and $R_{12}$ taken together form a 4-, 5-, or 6-membered heterocyclic ring;

G is

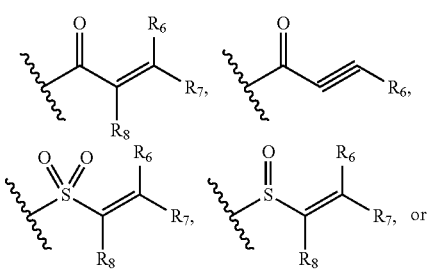

-continued

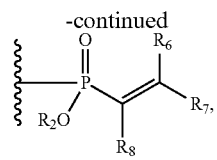

wherein,
$R_6$, $R_7$ and $R_8$ are independently selected from among H, lower alkyl or substituted lower alkyl, lower heteroalkyl or substituted lower heteroalkyl, substituted or unsubstituted lower cycloalkyl, and substituted or unsubstituted lower heterocycloalkyl; and
pharmaceutically acceptable active metabolites, pharmaceutically acceptable solvates, pharmaceutically acceptable salts, or pharmaceutically acceptable prodrugs thereof.

In some embodiments, the "G" group of any of Formula (A), Formula (B), or Formula (C) is any group that is used to tailor the physical and biological properties of the molecule. Such tailoring/modifications are achieved using groups which modulate Michael acceptor chemical reactivity, acidity, basicity, lipophilicity, solubility and other physical properties of the molecule. The physical and biological properties modulated by such modifications to G include, by way of example only, enhancing chemical reactivity of Michael acceptor group, solubility, in vivo absorption, and in vivo metabolism. In addition, in vivo metabolism may include, by way of example only, controlling in vivo PK properties, off-target activities, potential toxicities associated with cypP450 interactions, drug-drug interactions, and the like. Further, modifications to G allow for the tailoring of the in vivo efficacy of the compound through the modulation of, by way of example, specific and non-specific protein binding to plasma proteins and lipids and tissue distribution in vivo.

In some embodiments, the BTK inhibitor has the structure of Formula (D):

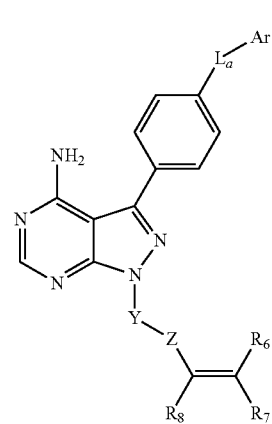

Formula (D)

wherein
La is $CH_2$, O, NH or S;
Ar is an optionally substituted aromatic carbocycle or an aromatic heterocycle;
Y is an optionally substituted alkyl, heteroalkyl, carbocycle, heterocycle, or combination thereof;
Z is C(O), OC(O), NHC(O), C(S), $S(O)_x$, $OS(O)_x$, $NHS(O)_x$, where x is 1 or 2; and
$R_6$, $R_7$, and $R_8$ are independently selected from H, alkyl, heteroalkyl, carbocycle, heterocycle, or combinations thereof.

In some embodiments, La is O.
In some embodiments, Ar is phenyl.
In some embodiments, Z is C(O).
In some embodiments, each of $R_1$, $R_2$, and $R_3$ is H.
In some embodiments, provided herein is a compound of Formula (D). Formula (D) is as follows:

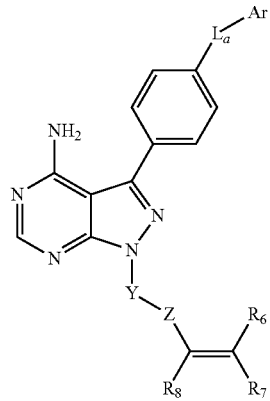

Formula (D)

wherein:
$L_a$ is $CH_2$, O, NH or S;
Ar is a substituted or unsubstituted aryl, or a substituted or unsubstituted heteroaryl;
Y is an optionally substituted group selected from among alkyl, heteroalkyl, cycloalkyl, heterocycloalkyl, aryl, and heteroaryl;
Z is C(=O), OC(=O), NHC(=O), C(=S), $S(=O)_x$, $OS(=O)_x$, $NHS(=O)_x$, where x is 1 or 2;
$R_7$ and $R_8$ are independently selected from among H, unsubstituted $C_1$-$C_4$alkyl, substituted $C_1$-$C_4$alkyl, unsubstituted $C_1$-$C_4$heteroalkyl, substituted $C_1$-$C_4$heteroalkyl, unsubstituted $C_3$-$C_6$cycloalkyl, substituted $C_3$-$C_6$cycloalkyl, unsubstituted $C_2$-$C_6$heterocycloalkyl, and substituted $C_2$-$C_6$heterocycloalkyl; or
$R_7$ and $R_8$ taken together form a bond;
$R_6$ is H, substituted or unsubstituted $C_1$-$C_4$alkyl, substituted or unsubstituted $C_1$-$C_4$heteroalkyl, $C_1$-$C_6$alkoxyalkyl, $C_1$-$C_8$alkylaminoalkyl, substituted or unsubstituted $C_3$-$C_6$cycloalkyl, substituted or unsubstituted aryl, substituted or unsubstituted $C_2$-$C_8$heterocycloalkyl, substituted or unsubstituted heteroaryl, $C_1$-$C_4$alkyl(aryl), $C_1$-$C_4$alkyl(heteroaryl), $C_1$-$C_4$alkyl($C_3$-$C_8$cycloalkyl), or $C_1$-$C_4$alkyl($C_2$-$C_8$heterocycloalkyl); and
pharmaceutically active metabolites, or pharmaceutically acceptable solvates, pharmaceutically acceptable salts, or pharmaceutically acceptable prodrugs thereof.

For any and all of the embodiments, substituents can be selected from among from a subset of the listed alternatives. For example, in some embodiments, $L_a$ is $CH_2$, O, or NH. In other embodiments, $L_a$ is O or NH. In yet other embodiments, $L_a$ is O.

In some embodiments, Ar is a substituted or unsubstituted aryl. In yet other embodiments, Ar is a 6-membered aryl. In some other embodiments, Ar is phenyl.

In some embodiments, x is 2. In yet other embodiments, Z is C(=O), OC(=O), NHC(=O), $S(=O)_x$, $OS(=O)_x$, or $NHS(=O)_x$. In some other embodiments, Z is C(=O), NHC(=O), or $S(=O)_2$.

In some embodiments, $R_7$ and $R_8$ are independently selected from among H, unsubstituted $C_1$-$C_4$ alkyl, substituted C₁-C₄alkyl, unsubstituted C₁-C₄heteroalkyl, and substituted C₁-C₄heteroalkyl; or R₇ and R₈ taken together form a bond. In yet other embodiments, each of R₇ and R₈ is H; or R₇ and R₈ taken together form a bond.

In some embodiments, R₆ is H, substituted or unsubstituted C₁-C₄alkyl, substituted or unsubstituted C₁-C₄heteroalkyl, C₁-C₆alkoxyalkyl, C₁-C₂alkyl-N(C₁-C₃alkyl)₂, substituted or unsubstituted aryl, substituted or unsubstituted heteroaryl, C₁-C₄alkyl(aryl), C₁-C₄alkyl(heteroaryl), C₁-C₄alkyl(C₃-C₈cycloalkyl), or C₁-C₄alkyl(C₂-C₈heterocycloalkyl). In some other embodiments, R₆ is H, substituted or unsubstituted C₁-C₄alkyl, substituted or unsubstituted C₁-C₄heteroalkyl, C₁-C₆alkoxyalkyl, C₁-C₂alkyl-N(C₁-C₃alkyl)₂, C₁-C₄alkyl(aryl), C₁-C₄alkyl(heteroaryl), C₁-C₄alkyl(C₃-C₈cycloalkyl), or C₁-C₄alkyl(C₂-C₈heterocycloalkyl). In yet other embodiments, R₆ is H, substituted or unsubstituted C₁-C₄alkyl, —CH₂—O—(C₁-C₃alkyl), —CH₂—N(C₁-C₃alkyl)₂, C₁-C₄alkyl(phenyl), or C₁-C₄alkyl(5- or 6-membered heteroaryl). In some embodiments, R₆ is H, substituted or unsubstituted C₁-C₄alkyl, —CH₂—O—(C₁-C₃alkyl), —CH₂—N(C₁-C₃alkyl)₂, C₁-C₄alkyl(phenyl), or C₁-C₄alkyl(5- or 6-membered heteroaryl containing 1 or 2 N atoms), or C₁-C₄alkyl(5- or 6-membered heterocycloalkyl containing 1 or 2 N atoms).

In some embodiments, Y is an optionally substituted group selected from among alkyl, heteroalkyl, cycloalkyl, and heterocycloalkyl. In other embodiments, Y is an optionally substituted group selected from among C₁-C₆alkyl, C₁-C₆heteroalkyl, 4-, 5-, 6- or 7-membered cycloalkyl, and 4-, 5-, 6- or 7-membered heterocycloalkyl. In yet other embodiments, Y is an optionally substituted group selected from among C₁-C₆alkyl, C₁-C₆heteroalkyl, 5-, or 6-membered cycloalkyl, and 5-, or 6-membered heterocycloalkyl containing 1 or 2 N atoms. In some other embodiments, Y is a 5-, or 6-membered cycloalkyl, or a 5-, or 6-membered heterocycloalkyl containing 1 or 2 N atoms.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In some embodiments the BTK inhibitor compounds of Formula (A), Formula (B), Formula (C), Formula (D), include, but are not limited to, compounds selected from the group consisting of:

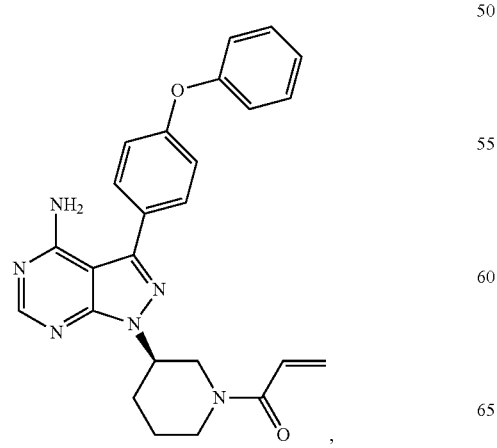

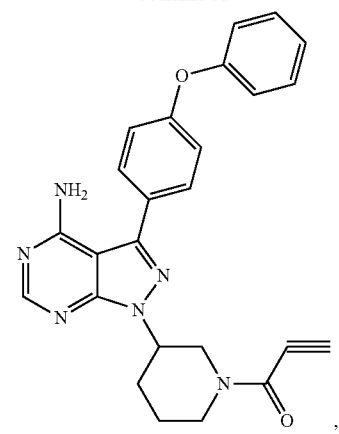

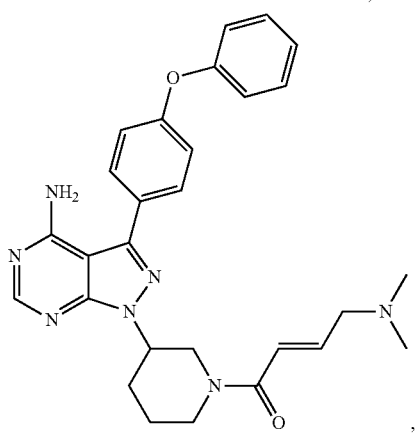

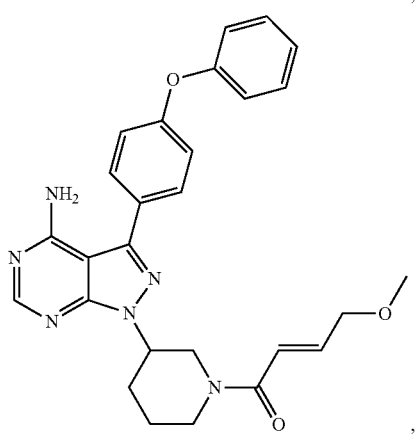

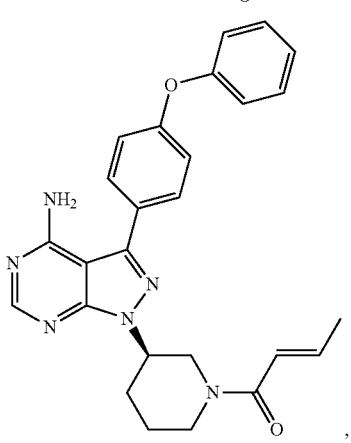

33
-continued
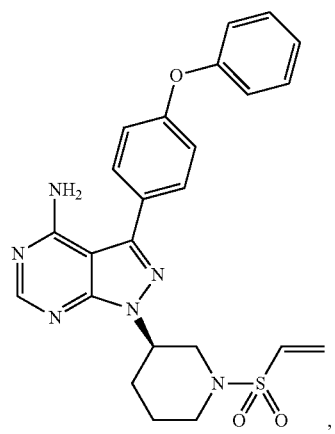
34
-continued
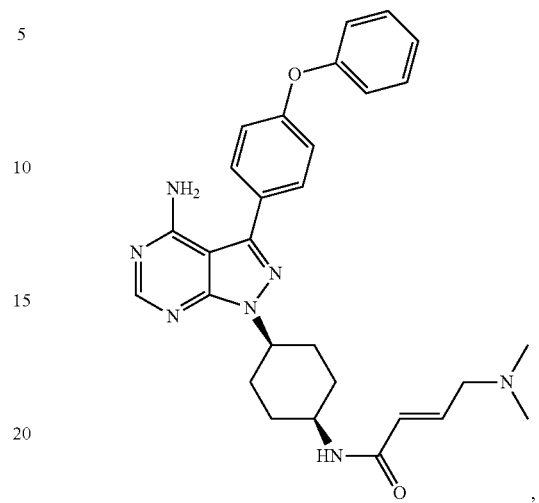
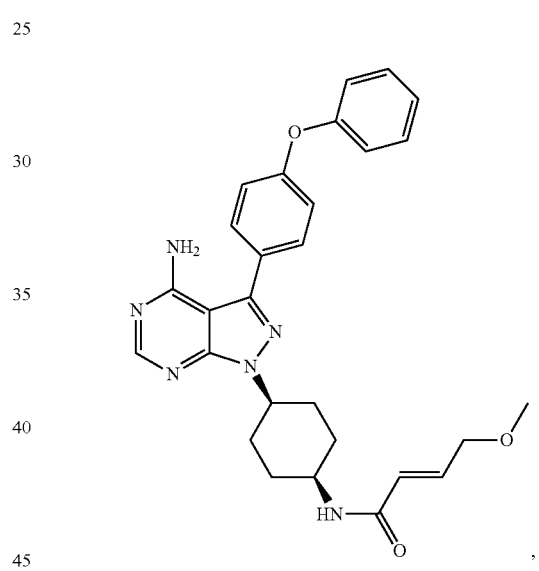
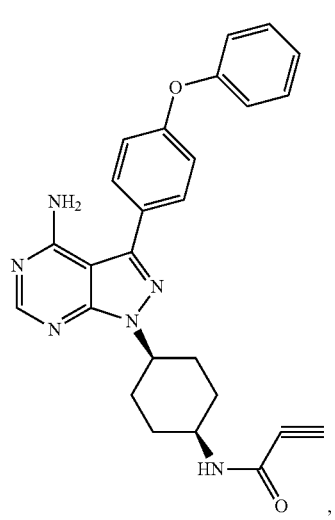
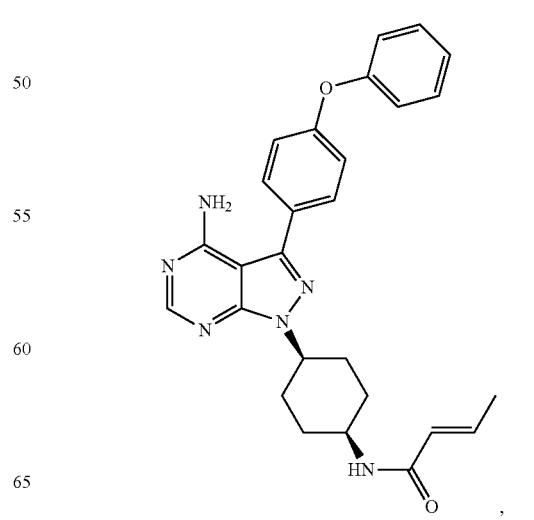

-continued
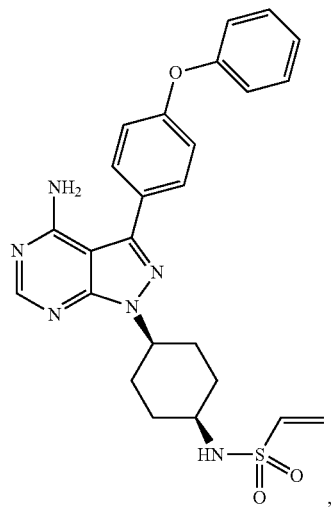
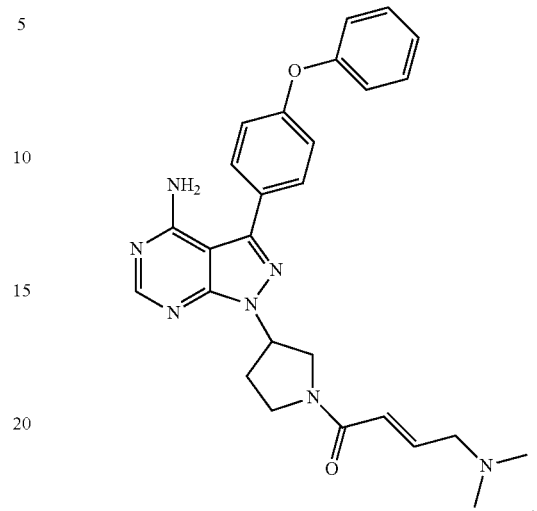
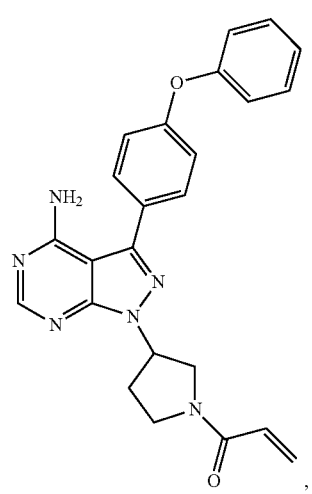
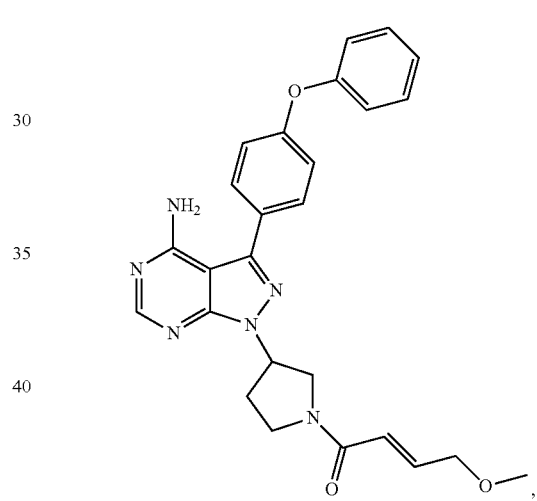
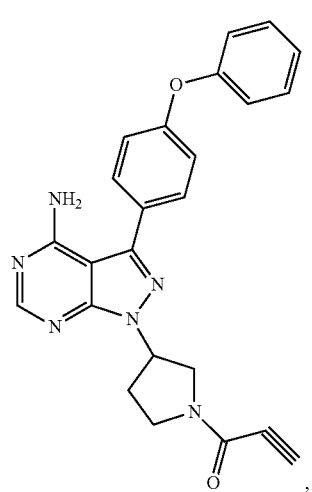
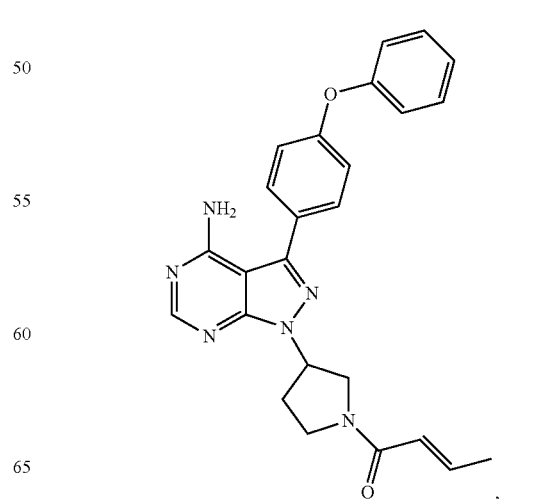

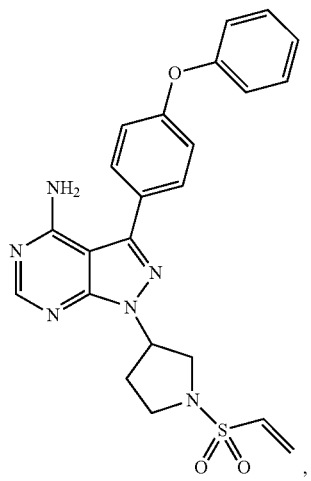,
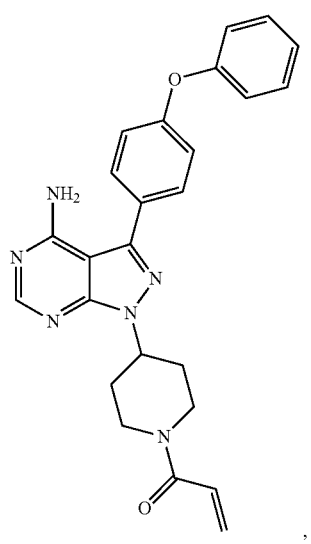,
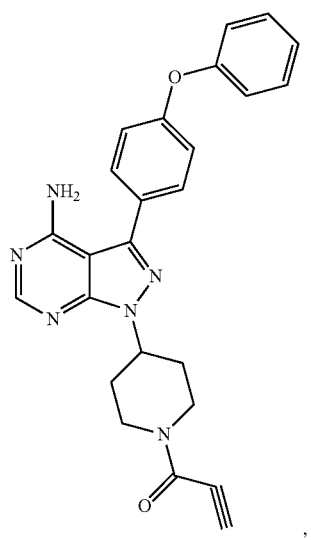,
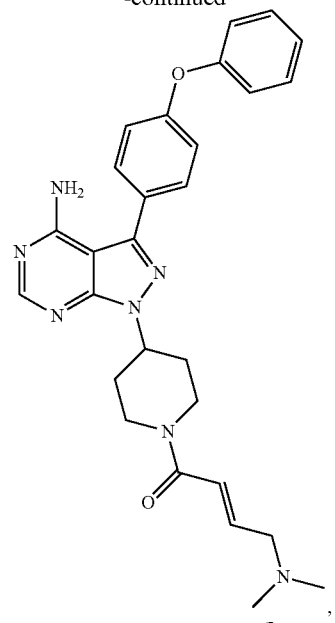,
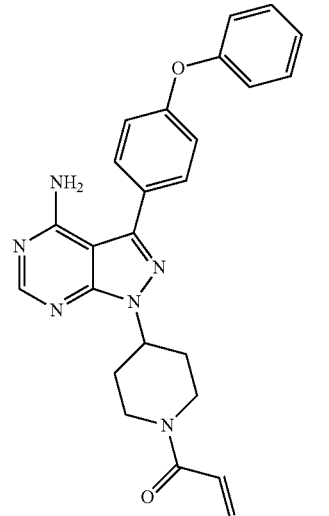,
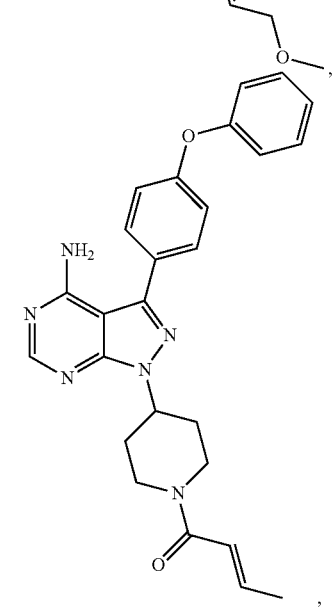,

39
-continued
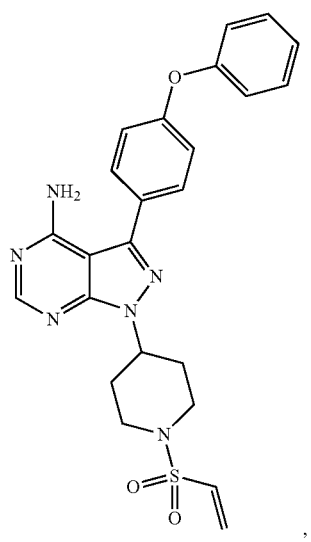
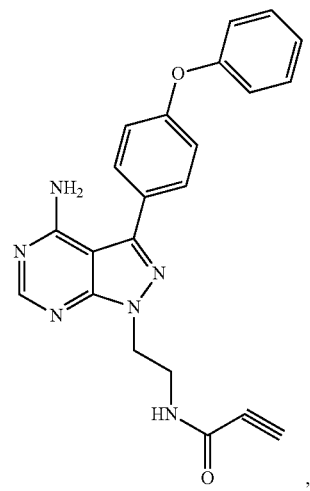
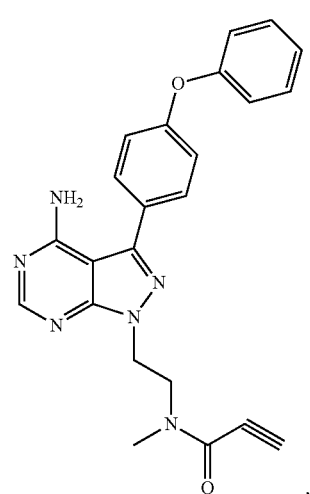
40
-continued
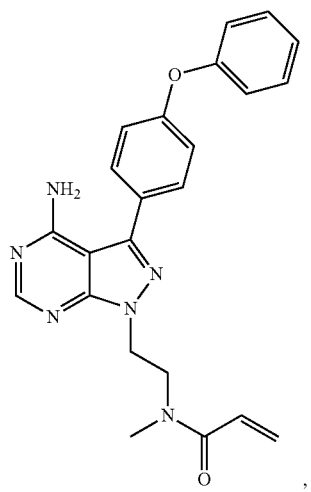
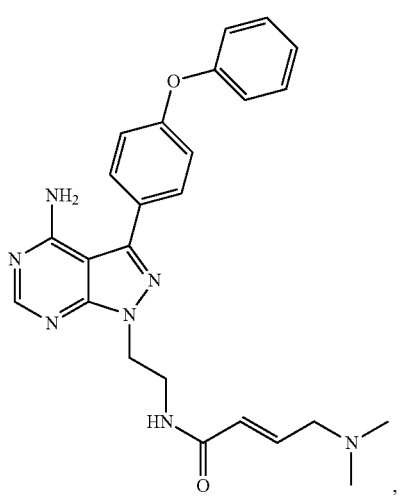

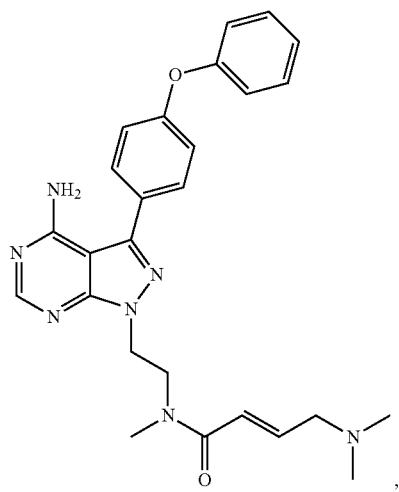
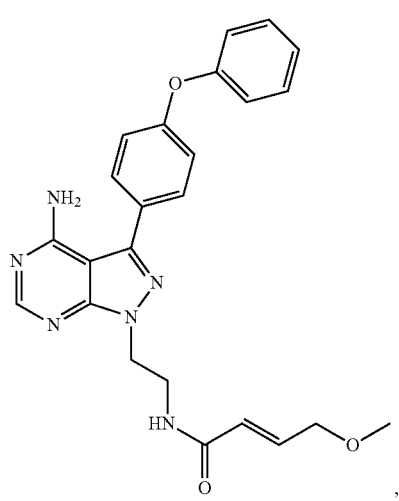
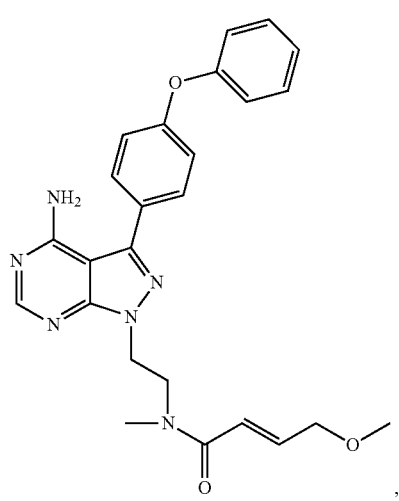
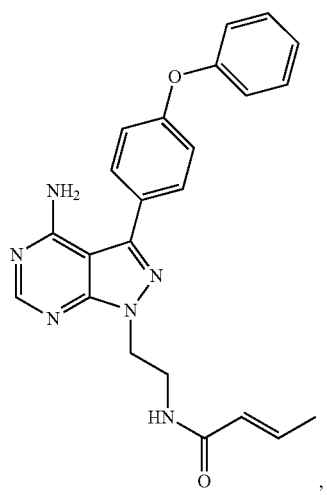
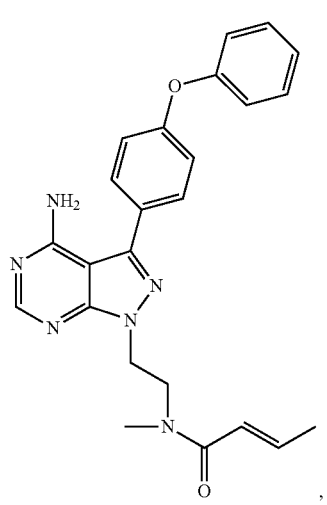
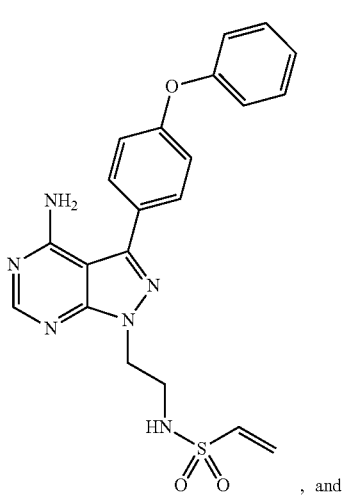
, and

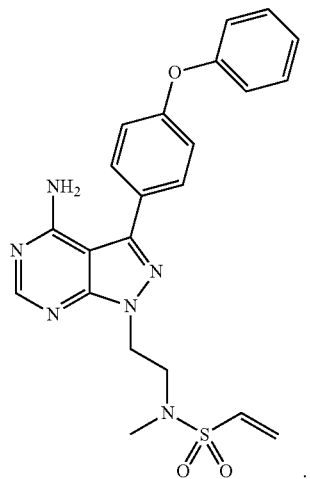
In some embodiments, the BTK inhibitor compounds are selected from among:
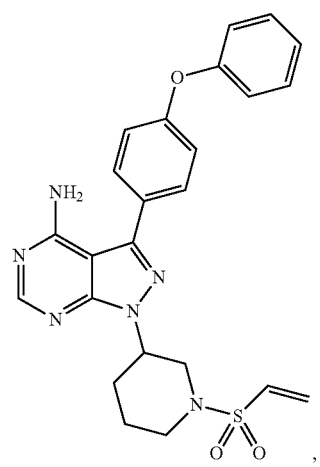
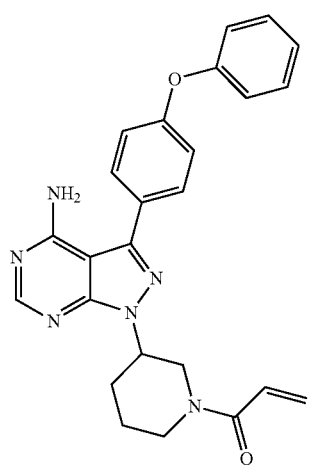
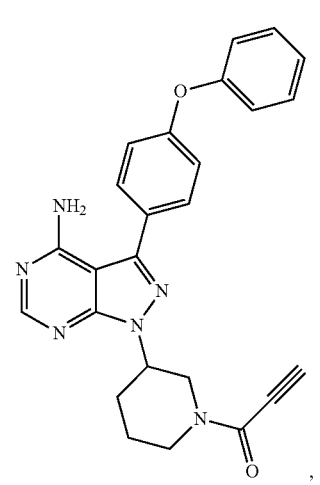
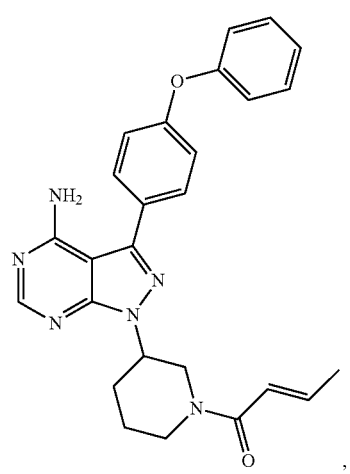
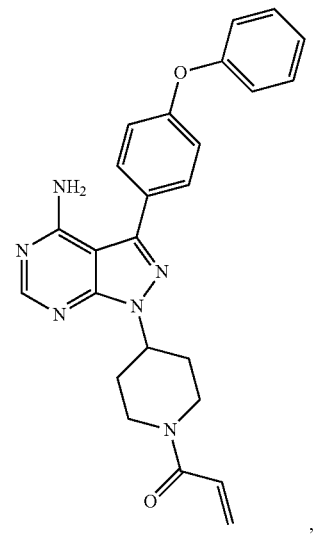 [SMILES: C#CC(=O)N1CCC(n2nc(-c3ccc(Oc4ccccc4)cc3)c3c(N)ncnc32)CC1]

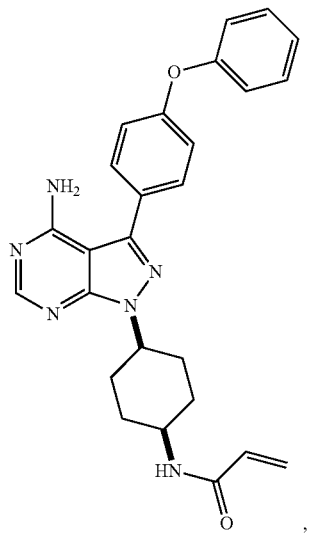

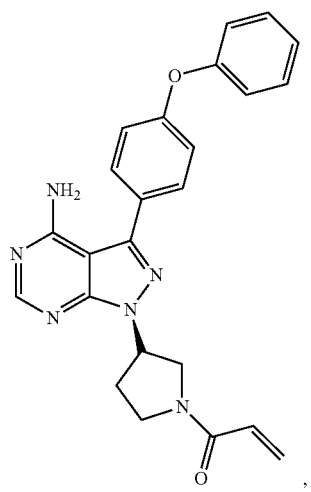

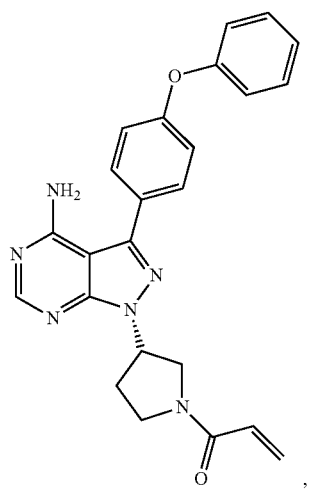

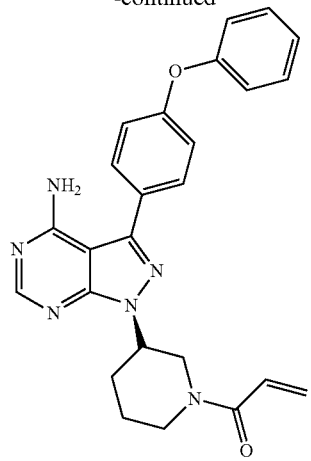

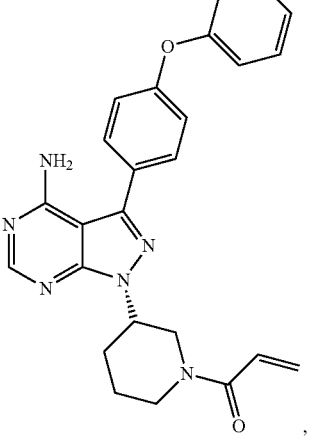

, and

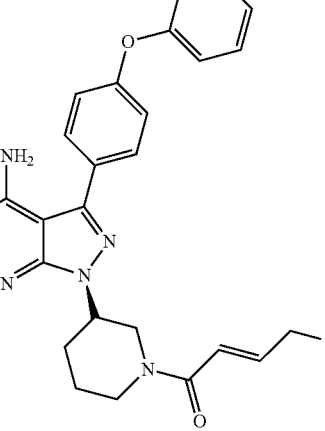

.

In some embodiments, the BTK inhibitor compounds are selected from among:
1-(3-(4-amino-3-(4-phenoxyphenyl)-1H-pyrazolo[3,4-d]pyrimidin-1-yl)piperidin-1-yl)prop-2-en-1-one (Compound 4); (E)-1-(3-(4-amino-3-(4-phenoxyphenyl)-1H-pyrazolo[3,4-d]pyrimidin-1-yl)piperidin-1-yl)but-2-en-1-one (Compound 5); 1-(3-(4-amino-3-(4-phenoxyphenyl)-1H-pyrazolo[3,4-d]pyrimidin-1-yl)piperidin-1-yl)sulfonylethene (Compound 6); 1-(3-(4-amino-3-(4-phenoxyphenyl)-1H-pyrazolo[3,4-d]pyrimidin-1-yl)piperidin-1-yl)prop-2-yn-1-one (Compound 8); 1-(4-(4-amino-3-(4-phenoxyphenyl)-1H-pyrazolo[3,4-d]pyrimidin-1-yl)piperidin-1-yl)prop-2-en-1-one (Compound 9); N-((1 s,4s)-4-(4-amino-3-(4-phenoxyphenyl)-1H-pyrazolo[3,4-d]pyrimidin-1-yl)cyclohexyl)acrylamide (Compound 10); 1-((R)-3-(4-amino-3-(4-phenoxyphenyl)-1H-pyrazolo[3,4-d]pyrimidin-1-yl)pyrrolidin-1-yl)prop-2-en-1-one (Compound 11); 1-((S)-3-(4-amino-3-(4-phenoxyphenyl)-1H-pyrazolo[3,4-d]pyrimidin-1-yl)pyrrolidin-1-yl)prop-2-en-1-one (Compound 12); 1-((R)-3-(4-amino-3-(4-phenoxyphenyl)-1H-pyrazolo[3,4-d]pyrimidin-1-yl)piperidin-1-yl)prop-2-en-1-one (Compound 13); 1-((S)-3-(4-amino-3-(4-phenoxyphenyl)-1H-pyrazolo[3,4-d]pyrimidin-1-yl)piperidin-1-yl)prop-2-en-1-one (Compound 14); and (E)-1-(3-(4-amino-3-(4-phenoxyphenyl)-1H-pyrazolo[3,4-d]pyrimidin-1-yl)piperidin-1-yl)-4-(dimethylamino)but-2-en-1-one (Compound 15).

Throughout the specification, groups and substituents thereof can be chosen by one skilled in the field to provide stable moieties and compounds.

The compounds of any of Formula (A), or Formula (B), or Formula (C), or Formula (D) can irreversibly inhibit Btk and may be used to treat patients suffering from Bruton's tyrosine kinase-dependent or Bruton's tyrosine kinase mediated conditions or diseases, including, but not limited to, cancer, autoimmune and other inflammatory diseases.

"Ibrutinib" or "1-((R)-3-(4-amino-3-(4-phenoxyphenyl)-1H-pyrazolo[3,4-d]pyrimidin-1-yl)piperidin-1-yl)prop-2-en-1-one" or "1-{(3R)-3-[4-amino-3-(4-phenoxyphenyl)-1H-pyrazolo[3,4-d]pyrimidin-1-yl]piperidin-1-yl}prop-2-en-1-one" or "2-Propen-1-one, 1-[(3R)-3-[4-amino-3-(4-phenoxyphenyl)-1H-pyrazolo[3,4-d]pyrimidin-1-yl]-1-piperidinyl-" or Ibrutinib or any other suitable name refers to the compound with the following structure:

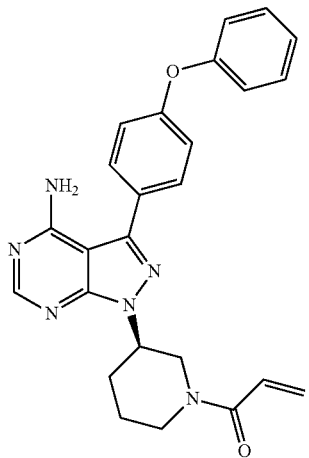 [SMILES: C=CC(=O)N1CCC[C@@H](n2nc(-c3ccc(Oc4ccccc4)cc3)c3c(N)ncnc32)C1]

A wide variety of pharmaceutically acceptable salts is formed from Ibrutinib and includes:
acid addition salts formed by reacting Ibrutinib with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like;

acid addition salts formed by reacting Ibrutinib with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Ibrutinib refers to a salt of Ibrutinib, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). Hydrates are formed when the solvent is water, or alcoholates are formed when the solvent is alcohol. In some embodiments, solvates of Ibrutinib, or pharmaceutically acceptable salts thereof, are conveniently prepared or formed during the processes described herein. In some embodiments, solvates of Ibrutinib are anhydrous. In some embodiments, Ibrutinib, or pharmaceutically acceptable salts thereof, exist in unsolvated form. In some embodiments, Ibrutinib, or pharmaceutically acceptable salts thereof, exist in unsolvated form and are anhydrous.

In yet other embodiments, Ibrutinib, or a pharmaceutically acceptable salt thereof, is prepared in various forms, including but not limited to, amorphous phase, crystalline forms, milled forms and nano-particulate forms. In some embodiments, Ibrutinib, or a pharmaceutically acceptable salt thereof, is amorphous. In some embodiments, Ibrutinib, or a pharmaceutically acceptable salt thereof, is amorphous and anhydrous. In some embodiments, Ibrutinib, or a pharmaceutically acceptable salt thereof, is crystalline. In some embodiments, Ibrutinib, or a pharmaceutically acceptable salt thereof, is crystalline and anhydrous.

In some embodiments, Ibrutinib is prepared as outlined in U.S. Pat. No. 7,514,444.

In some embodiments, the Btk inhibitor is PCI-45292, PCI-45466, AVL-101/CC-101 (Avila Therapeutics/Celgene Corporation), AVL-263/CC-263 (Avila Therapeutics/Celgene Corporation), AVL-292/CC-292 (Avila Therapeutics/Celgene Corporation), AVL-291/CC-291 (Avila Therapeutics/Celgene Corporation), CNX 774 (Avila Therapeutics), BMS-488516 (Bristol-Myers Squibb), BMS-509744 (Bristol-Myers Squibb), CGI-1746 (CGI Pharma/Gilead Sciences), CGI-560 (CGI Pharma/Gilead Sciences), CTA-056, GDC-0834 (Genentech), HY-11066 (also, CTK417891, HMS3265G21, HMS3265G22, HMS3265H21, HMS3265H22, 439574-61-5, AG-F-54930), ONO-4059 (Ono Pharmaceutical Co., Ltd.), ONO-WG37 (Ono Pharmaceutical Co., Ltd.), PLS-123 (Peking University), RN486 (Hoffmann-La Roche), HM71224 (Hanmi Pharmaceutical Company Limited), LFM-A13, BGB-3111 (Beigene), KBP- 7536 (KBP BioSciences), ACP-196 (Acerta Pharma) and JTE-051 (Japan Tobacco Inc).

In some embodiments, the BTK inhibitor is 4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide (CGI-1746); 7-benzyl-1-(3-(piperidin-1-yl)propyl)-2-(4-(pyridin-4-yl)phenyl)-1H-imidazo[4,5-g]quinoxalin-6(5H)-one (CTA-056); (R)—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (GDC-0834); 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (RN-486); N-[5-[5-(4-acetylpiperazine-1-carbonyl)-4-methoxy-2-methylphenyl]sulfanyl-1,3-thiazol-2-yl]-4-[(3,3-dimethylbutan-2-ylamino)methyl]benzamide (BMS-509744, HY-11092); or N-(5-(((5-(4-Acetylpiperazine-1-carbonyl)-4-methoxy-2-methylphenyl)thio)thiazol-2-yl)-4-(((3-methylbutan-2-yl)amino)methyl)benzamide (HY11066); or a pharmaceutically acceptable salt thereof.

In some embodiments, the BTK inhibitor is:

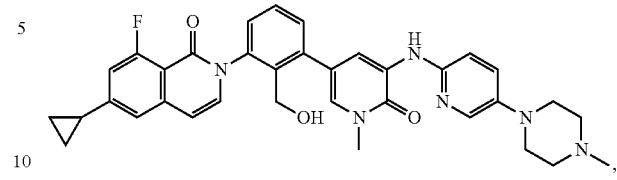

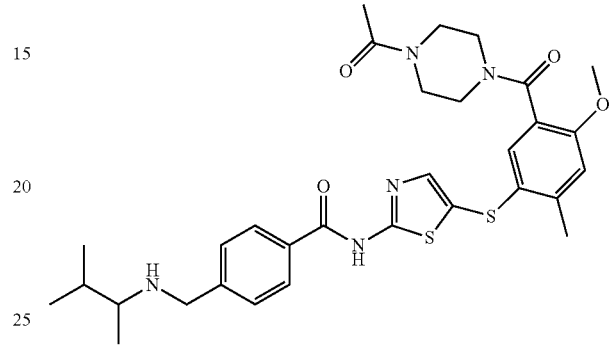

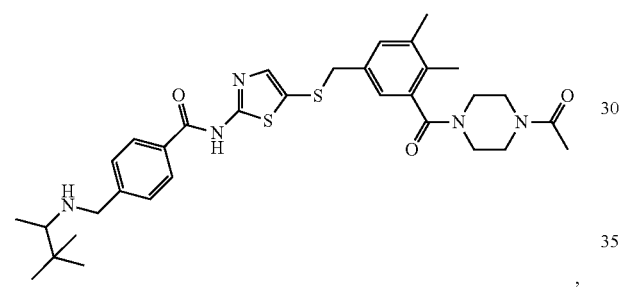

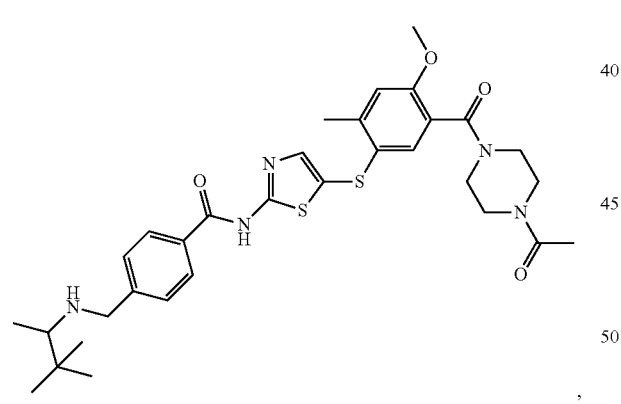

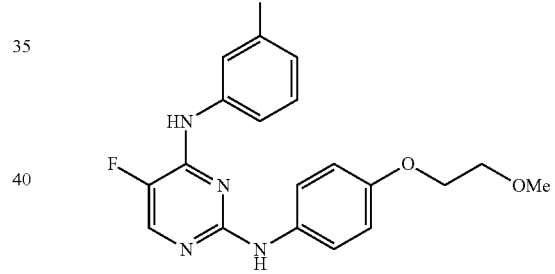

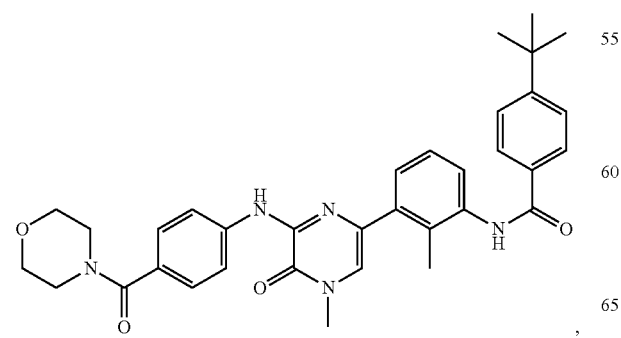

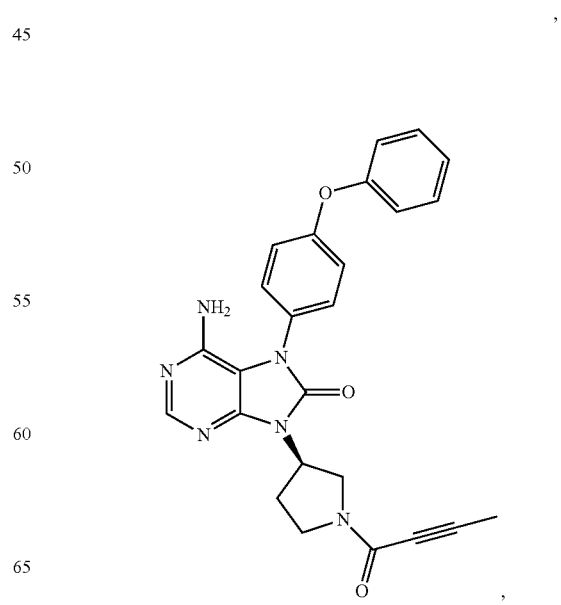

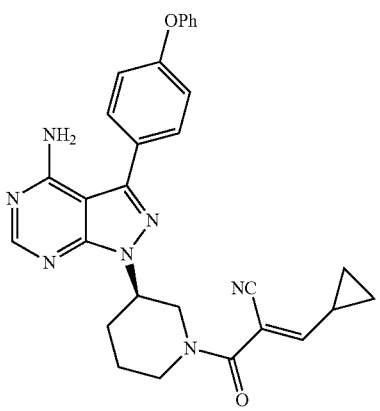
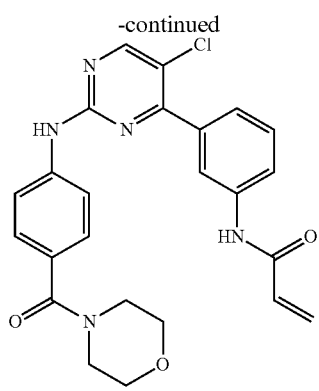
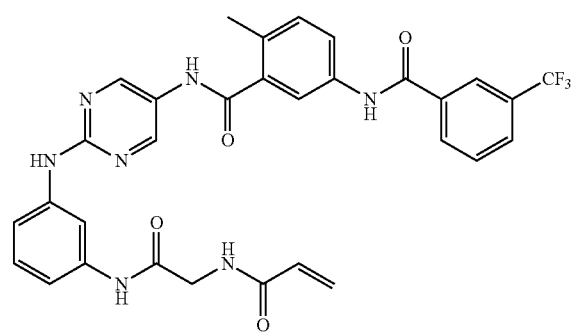
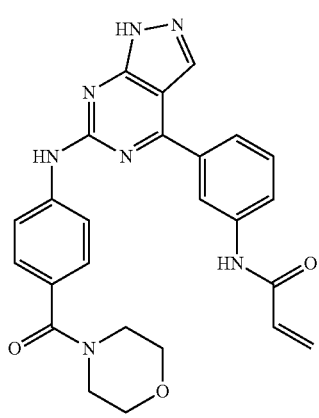
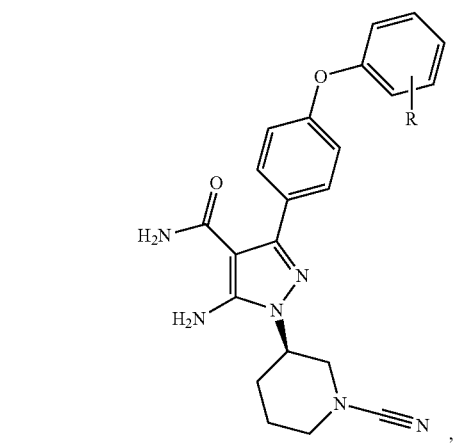
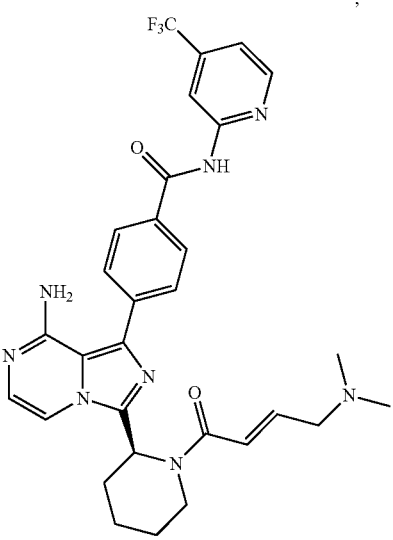
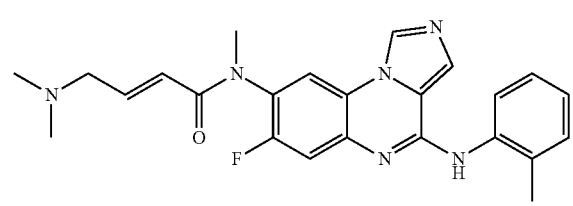
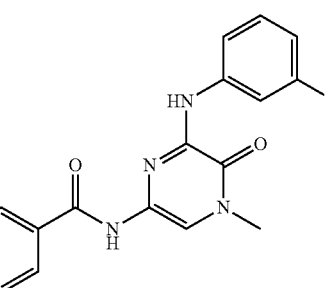

53

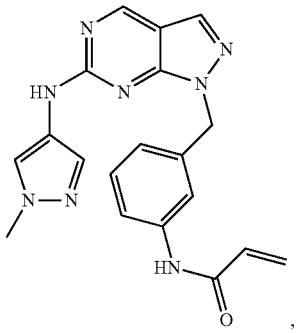

,

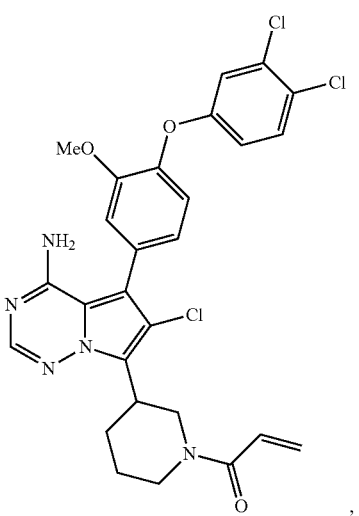

,

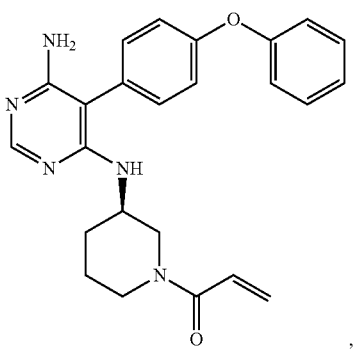

,

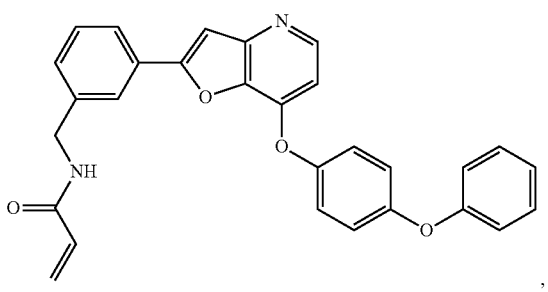

, or

54

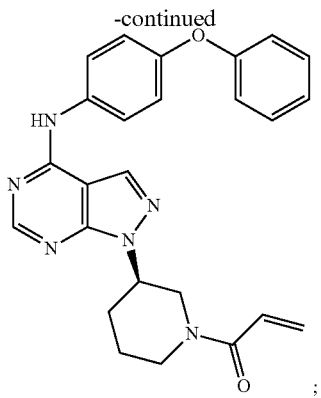

;

or a pharmaceutically acceptable salt thereof.

ITK Inhibitors

In some embodiments, ACK inhibitor is an ITK inhibitor. In some embodiments, the ITK inhibitor covalently binds to Cysteine 442 of ITK. In some embodiments, the ITK inhibitor is an ITK inhibitor compound described in WO2002/0500071, which is incorporated by reference in its entirety. In some embodiments, the ITK inhibitor is an ITK inhibitor compound described in WO2005/070420, which is incorporated by reference in its entirety. In some embodiments, the ITK inhibitor is an ITK inhibitor compound described in WO2005/079791, which is incorporated by reference in its entirety. In some embodiments, the ITK inhibitor is an ITK inhibitor compound described in WO2007/076228, which is incorporated by reference in its entirety. In some embodiments, the ITK inhibitor is an ITK inhibitor compound described in WO2007/058832, which is incorporated by reference in its entirety. In some embodiments, the ITK inhibitor is an ITK inhibitor compound described in WO2004/016610, which is incorporated by reference in its entirety. In some embodiments, the ITK inhibitor is an ITK inhibitor compound described in WO2004/016611, which is incorporated by reference in its entirety. In some embodiments, the ITK inhibitor is an ITK inhibitor compound described in WO2004/016600, which is incorporated by reference in its entirety. In some embodiments, the ITK inhibitor is an ITK inhibitor compound described in WO2004/016615, which is incorporated by reference in its entirety. In some embodiments, the ITK inhibitor is an ITK inhibitor compound described in WO2005/026175, which is incorporated by reference in its entirety. In some embodiments, the ITK inhibitor is an ITK inhibitor compound described in WO2006/065946, which is incorporated by reference in its entirety. In some embodiments, the ITK inhibitor is an ITK inhibitor compound described in WO2007/027594, which is incorporated by reference in its entirety. In some embodiments, the ITK inhibitor is an ITK inhibitor compound described in WO2007/017455, which is incorporated by reference in its entirety. In some embodiments, the ITK inhibitor is an ITK inhibitor compound described in WO2008/025820, which is incorporated by reference in its entirety. In some embodiments, the ITK inhibitor is an ITK inhibitor compound described in WO2008/025821, which is incorporated by reference in its entirety. In some embodiments, the ITK inhibitor is an ITK inhibitor compound described in WO2008/025822, which is incorporated by reference in its entirety. In some embodiments, the ITK inhibitor is an ITK inhibitor compound described in WO2011/017219, which is incorporated by reference in its entirety. In some embodiments, the ITK inhibitor is an ITK inhibitor compound described in WO2011/090760, which is incorporated by reference in its entirety. In some embodiments, the ITK inhibitor is an ITK inhibitor compound described in WO2009/158571, which is incorporated by reference in its entirety. In some embodiments, the ITK inhibitor is an ITK inhibitor compound described in WO2009/051822, which is incorporated by reference in its entirety. In some embodiments, the Itk inhibitor is an Itk inhibitor compound described in US20110281850, which is incorporated by reference in its entirety. In some embodiments, the Itk inhibitor is an Itk inhibitor compound described in WO2014/082085, which is incorporated by reference in its entirety. In some embodiments, the Itk inhibitor is an Itk inhibitor compound described in WO2014/093383, which is incorporated by reference in its entirety. In some embodiments, the Itk inhibitor is an Itk inhibitor compound described in U.S. Pat. No. 8,759,358, which is incorporated by reference in its entirety. In some embodiments, the Itk inhibitor is an Itk inhibitor compound described in WO2014/105958, which is incorporated by reference in its entirety. In some embodiments, the Itk inhibitor is an Itk inhibitor compound described in US2014/0256704, which is incorporated by reference in its entirety. In some embodiments, the Itk inhibitor is an Itk inhibitor compound described in US20140315909, which is incorporated by reference in its entirety. In some embodiments, the Itk inhibitor is an Itk inhibitor compound described in US20140303161, which is incorporated by reference in its entirety. In some embodiments, the Itk inhibitor is an Itk inhibitor compound described in WO2014/145403, which is incorporated by reference in its entirety.

In some embodiments, the ITK inhibitor has a structure selected from:

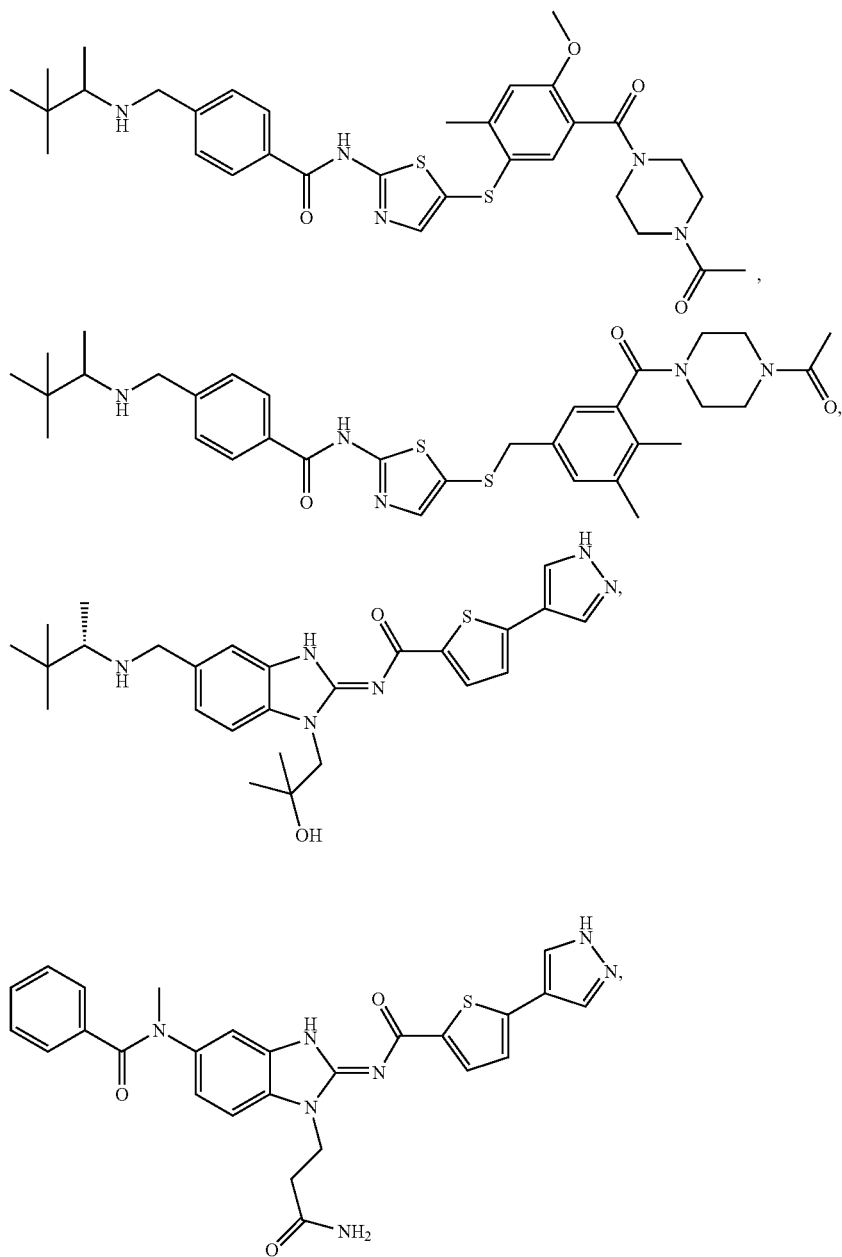

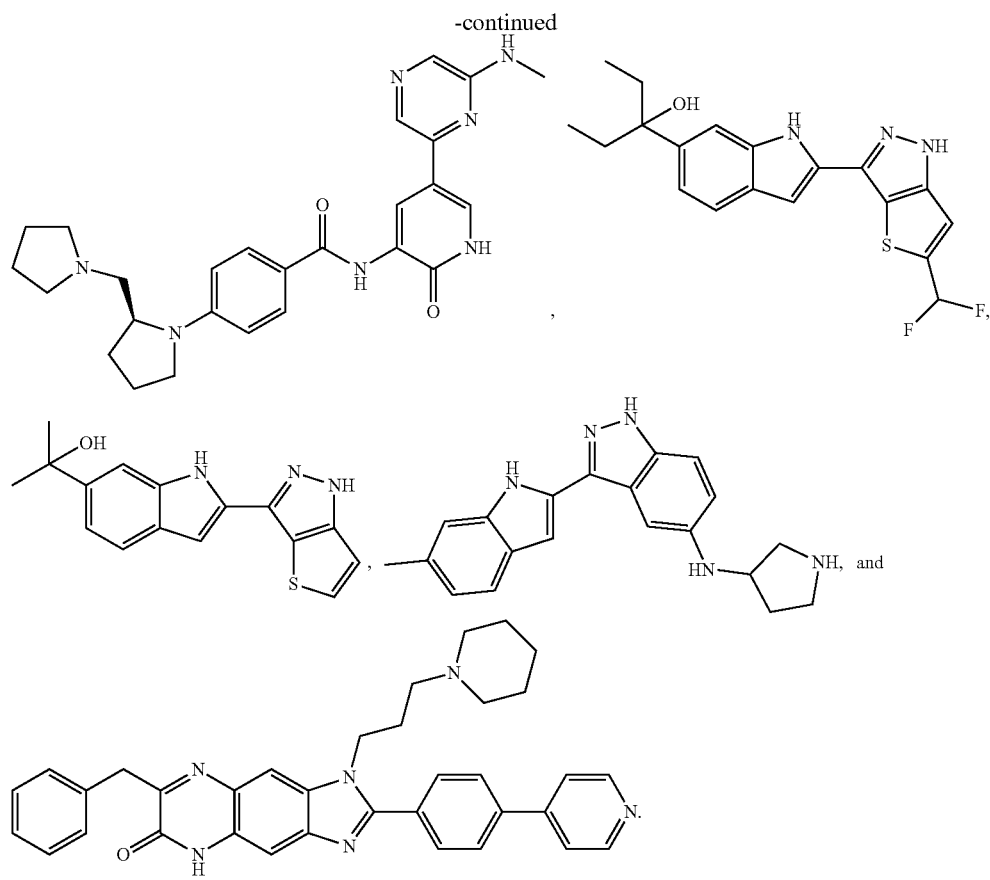

EXAMPLES

Example 1

PCI-32765 (also known as ibrutinib), a novel inhibitor of Bruton's tyrosine kinase (Btk) was a potent systemic mast cell blocker in the mouse model of insulinoma. As such, ibrutinib and ibrutinib in combination with an additional therapeutic agent were studied in a pre-clinical model of PDAC.

Immunohistochemistry & Collagen Staining

For immunohistochemical analyses, tissue samples were fixed overnight in neutral pH-buffered formalin, embedded in paraffin and sectioned (5 μm). Sections were then deparaffinized, rehydrated and microwaved for 1 min in 0.01 M citrate buffer (pH 6.0) for antigen retrieval. Primary antibodies (rat monoclonal anti-CD11b (clone M1/70), eBioscience; rabbit monoclonal anti-Ki67 (clone SP6), Neomarkers) were applied for 2 h in blocking buffer (2.5% BSA, 5% goat serum and 0.3% Triton X-100 in PBS), followed by Vectastain ABC kit and DAB reagents (Vector Laboratories). Images were obtained with an Axiovert S100 TV inverted fluorescence microscope (Zeiss) and Open Lab 3.5.1 software, or with an Axiovert 100 inverted microscope (Zeiss) equipped with a Hamamatsu Orca digital camera. The mast cells were identified using 1% toluidine blue dissolved in ethanol. Picrosirius Red stain kit (Polysciences, Inc.) was used to stain for collagen Types I and III according to manufacturer instructions.

Flow Cytometry

Following resection, PDAC tumors isolated from PBS-perfused mice were immediately placed in ice-cold PBS, followed by manual mincing using scissors and a 20 min enzymatic digestion with 1.25 mg/mL collagenase type IV (Roche), 0.1% trypsin inhibitor, and 50 U/ml DNase I (Roche) in serum-free Dulbecco's Modified Eagle's Medium (DMEM) (Invitrogen) at 37° C. with continuous stirring. Single cell suspensions were then prepared by passing tissue through 70 μm nylon strainers (BD Biosciences). Cells were incubated for 30 min at 4° C. with rat anti-mouse CD16/CD32 mAb (1:250, clone 2.4 G2, BD Bioscience) in PBS, which also contained Live/Dead Aqua stain (1:250, Invitrogen) to differentiate between viable and dead cells. Cells were then incubated for 30 min in PBS containing 1.0% BSA (Sigma) and 2 mM EDTA with 100 μl of fluorophore-conjugated anti-mouse antibodies (dilution; clone): PE-Cy7-CD45 (1:800; 30-F11), PerCp-Cy5.5-CD3e (1:400; 145-2C11), PerCp-Cy5.5-CD19 (1:200; 6D5), PerCp-Cy5.5-CD49b (1:400; DX5), Alexa 700-CD11b (1:400; M1/70), APC780-CD11c (1:200; N418), eFluor450-MHCII (1:800; M5/114.15.2), APC-Ly6C (1:800; HK1.4), PE-Ly6G (1:400; 1A8), and PE-Cy5-F4/80 (1:400; BM8) (eBioscience or Biolegend). Cells were then washed once in PBS containing 1.0% BSA (Sigma) and 2 mM EDTA, followed by fixation with BD Cytofix for 30 min on ice. Following a final wash the cells were stored at 4° C. until data acquisition using a LSRII using FACSDiva software (BD Biosciences). Analysis was performed using FlowJo software program (Tree Star Inc).

Animal Studies

Mice were housed and treated following the protocols approved by the Institutional Animal Care and Use Committee (IACUC) at the University of California, San Francisco (UCSF) and by the CEEA (Ethical Committee for the Use of Experimental Animals) at the Vall d'Hebron Institute of Oncology (VHIO), Barcelona.

For all experiments, 8 week old male and female p53$^{ER/ER}$; LSLKRas$^{G12D}$; pdx1-Cre mice of mixed C57BL/6-FVB/N background were randomized into two groups: treated and control. Ibrutinib (0.16 mg/mL with 1% 2-Hydroxypropyl-beta-cyclodextrin (HP-β-CD)) was added to the drinking water of treated animals, and control animals received water containing vehicle only (1% HP-β-CD). Gemcitabine (75 mg/kg) was injected intraperitoneally twice a week for 3 weeks followed by a 1-week rest period. Sodium cromoglycate (10/kg) was dissolved in saline solution and injected intraperitoneally, and control mice were treated with vehicle only. Endpoint criteria were defined as 20% body weight loss in addition to general morbidity and lethargy caused by tumor burden. Mice euthanized due to intestinal metaplasia or mucocutaneous papillomas caused by extrapancreatic KRAS$^{G12D}$ expression were excluded from the survival study.

NOD/SCID mice were purchased from Charles River Laboratory. The anonymized human sample employed was part of the tissue biological material of the University Hospital Vall d'Hebron. The sample had been collected with a signed patient consent form and its use had been approved by the Ethics Committee (CEI) of the Hospital. The sample was randomly selected among the patient samples available. Heterotopic xenografts were generated from a tumor biopsy of a patient that underwent pancreatectomy at University Hospital Vall d'Hebron: when routine pathological gross examination of a resected pancreas led to the detection of an adenocarcinoma, a slice with a thickness of 1-2 mm was transferred to RPMI 1640 media containing Antibiotic-Antimycotic (Gibco) and kept on ice; within approximately 30 min the tissue sample was cut into pieces of 15 mm$^3$ under sterile conditions, suspended in Matrigel (BD Biosciences) and transported to the SPF area of the animal facility. A tumor piece was implanted subcutaneously into the flank of 2-3 female 6-week-old NOD/SCID mice. When successfully grafted tumors reached a size of about 750 mm$^3$ they were transplanted. The xenograft used for the study described here was transplanted to 6-week-old NOD/SCID females in generation 4, which after 6 weeks had produced a cohort of 12 mice with tumors measurable by caliper. Animals were randomized into 2 groups, 1 treated with ibrutinib and the other untreated. Tumor size was evaluated weekly by caliper measurements and tumor volume calculated using the following formula:

$$volume = \frac{length \times width^2}{2}$$

When tumor volume reached 1500 mm$^3$ animals were euthanized and the tumor was collected and fixed overnight in neutral pH-buffered formalin.

All the animal studies were performed in accordance with the ARRIVE guidelines and the 3 Rs rule of Replacement, Reduction and Refinement principles.

Statistics

Statistical analysis was carried out by two-tailed Mann-Whitney test (for IHC counts), two tailed unpaired t-test (for flow cytometry data) and Log-Rank test (for Kaplan-Meier survival curves). Standard error (±SEM) and standard deviation (±SD) are either represented in the graphs or following the means of all measures, as stated in brief description of the drawings. Statistical analysis was performed using GraphPad Prism 4.

Ibrutinib Affected the Tumor Microenvironment in PDAC

A p53$^{ER/ER}$; LSLKRas$^{G12D}$; pdx1-Cre mouse model that harbors a Cre-activated KRasG12D allele inserted into the endogenous KRas locus combined with pancreas-specific PDX-1-driven Cre recombinase activity was used. The disruption of Trp53 signaling in combination with KRas mutation leads to rapid tumorigenesis and histopathological features typical of human pancreatic adenocarcinoma within only 8 weeks. At this stage the animals were treated with ibrutinib, at a dose of 25 mg/Kg/day added to their drinking water, or with vehicle control. The animals were euthanized 4 weeks later and their pancreata harvested for analysis. Mast cells were recruited to the tumor stroma, but their degranulation was efficiently inhibited by ibrutinib treatment. This latter effect was corroborated with toluidine blue staining of pancreatic observed to be intact and displayed concentrated, intense staining. In stained, vehicle-treated mast cells, the cell borders were broken and the content of their granules were released. Furthermore, tumors treated with ibrutinib displayed a reduction in proliferation rate (FIG. 1A; 67.8±29.5% in untreated vs. 14.9±7.0% treated animals).

Figure 1B:
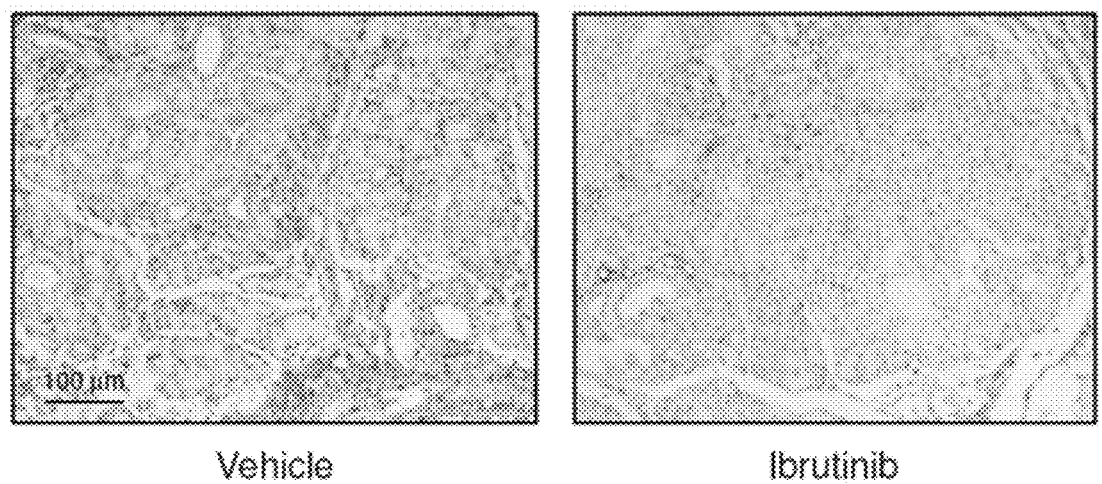
Figure 1C:
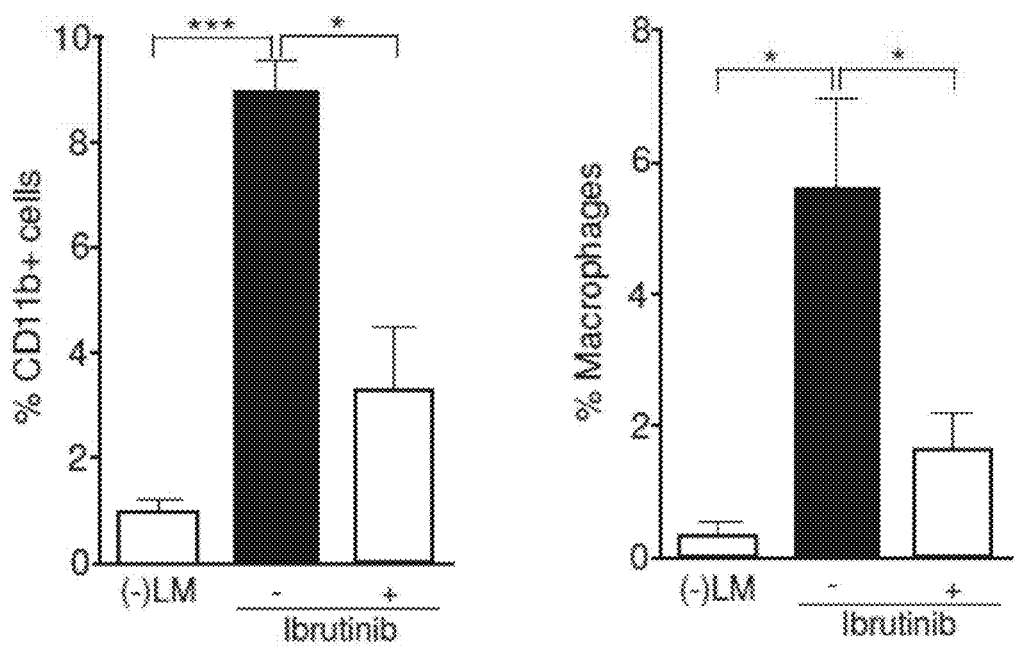
Figure 1D:
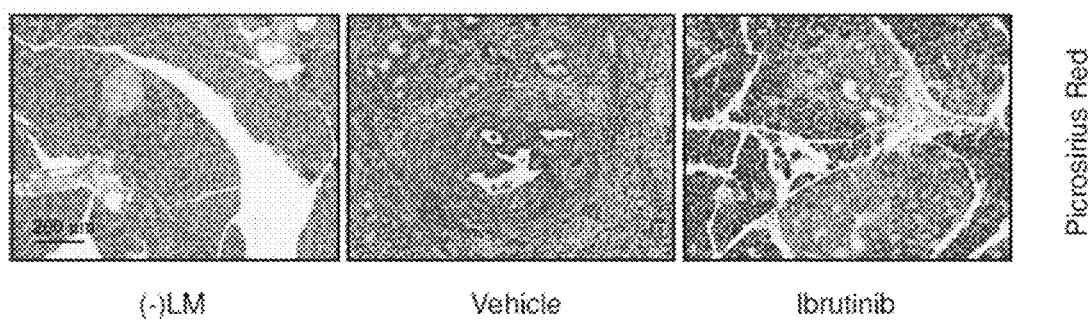

Their stroma were also affected, specifically in terms of CD11b positive cells, as shown by immunohistochemistry (FIG. 1B) and confirmed by FACS analysis (FIG. 1C, left panel). This latter analysis also showed a significant reduction in F4/80 positive macrophages (FIG. 1C, right panel). Reasons for this phenomenon can include the fact that several chemokines produced by mast cells, such as IL6, are known to be potent stimulants for monocytic cell migration and macrophage activation, so that inhibiting mast cells could prevent their recruitment. In addition, treatment with ibrutinib reduced the amount of collagen present in the tumors (FIG. 1D).

The Anti-Fibrotic Effect of Ibrutinib was Mast Cell Dependent

Figure 2A:
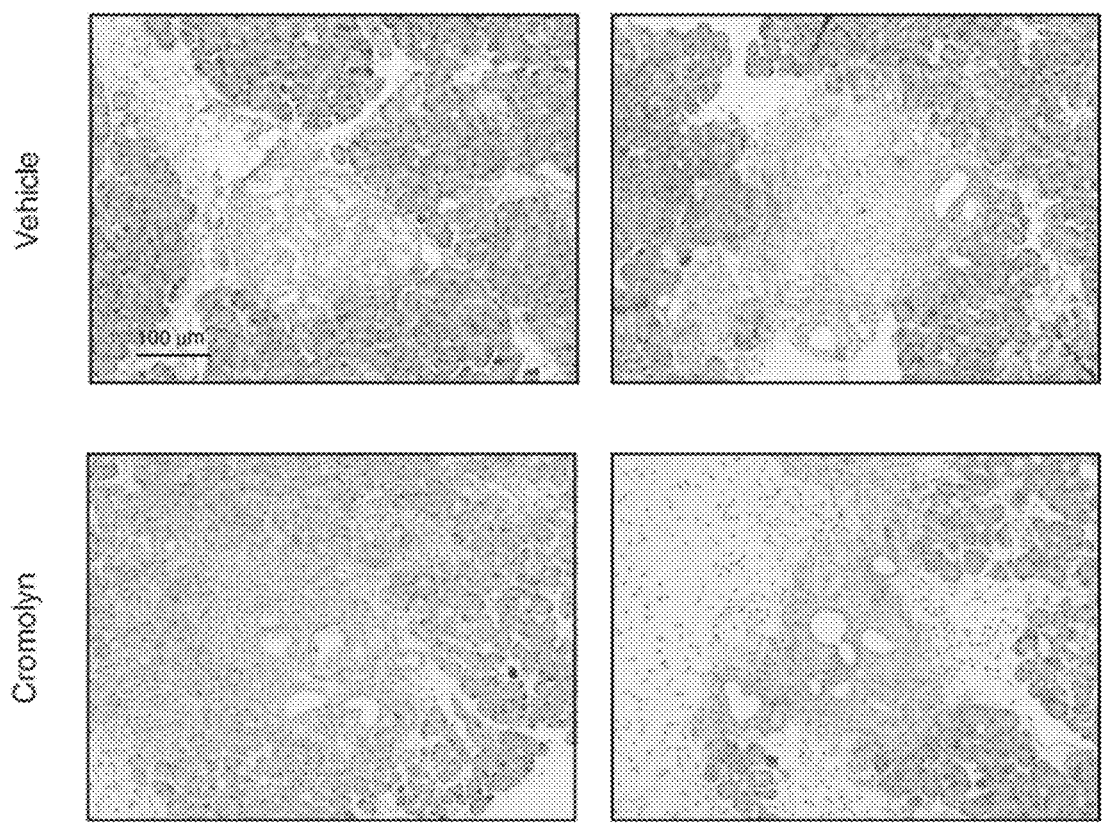
FIG. 2A and FIG. 2B illustrate mast cell function which is responsible for tissue fibrosis.

In order to verify that this effect on fibrosis was specifically due to mast cell interference, two independent control experiments were performed. In the first experiment, sodium cromoglycate (cromolyn), a well-characterized blocker of mast cell degranulation and inflammogen release was used. The p53$^{ER/ER}$; LSLKRas$^{G12D}$; pdx1-Cre mice were treated intraperitoneally (i.p.) with a daily injection of 10 mg per kg (bodyweight) of cromolyn, starting at 8 weeks of age. The animals were euthanized 4 weeks later and their pancreata analysed. Treatment with sodium cromoglicate recapitulated the antifibrotic effect displayed by ibrutinib (FIG. 2A). Furthermore, this finding showed that mast cells could exacerbate the cellular and extracellular dynamics of the tumor microenvironment found in PDAC.

Figure 2B:
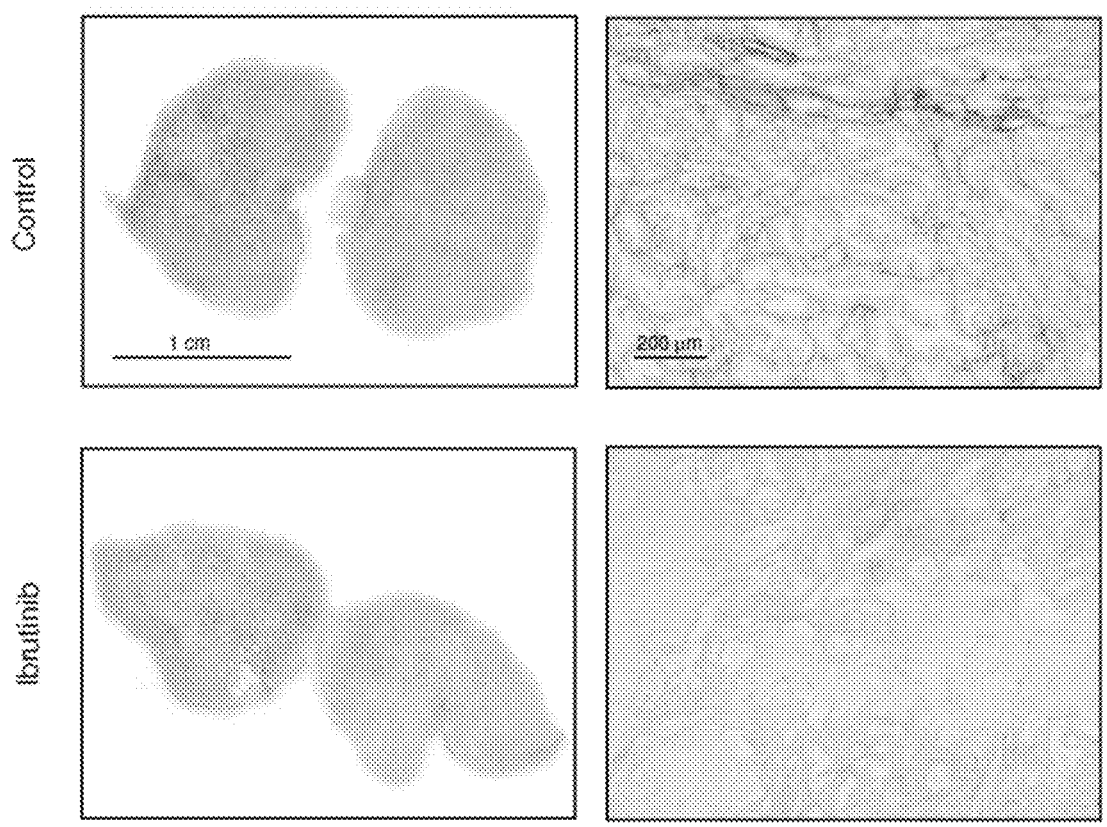

In the second experiment, subcutaneous xenografts (PDX) of a patient-derived tumor in NOD/SCID mice (FIG. 2B) were used. These mice are defective for both B and T cell function. Treatment with ibrutinib led to a reduction in tissue fibrosis (FIG. 2B), excluding B and T cell signaling modulation as ibrutinib's main mechanism of action in this context.

These two experiments showed that mast cells are involved in stimulating collagen deposition, consistent with data showing that mast cell tryptase might sustain liver fibrosis by promoting stellate cell proliferation and collagen synthesis and with the concept that mast cells could be the culprit in various fibrotic diseases.

Figure 3A:
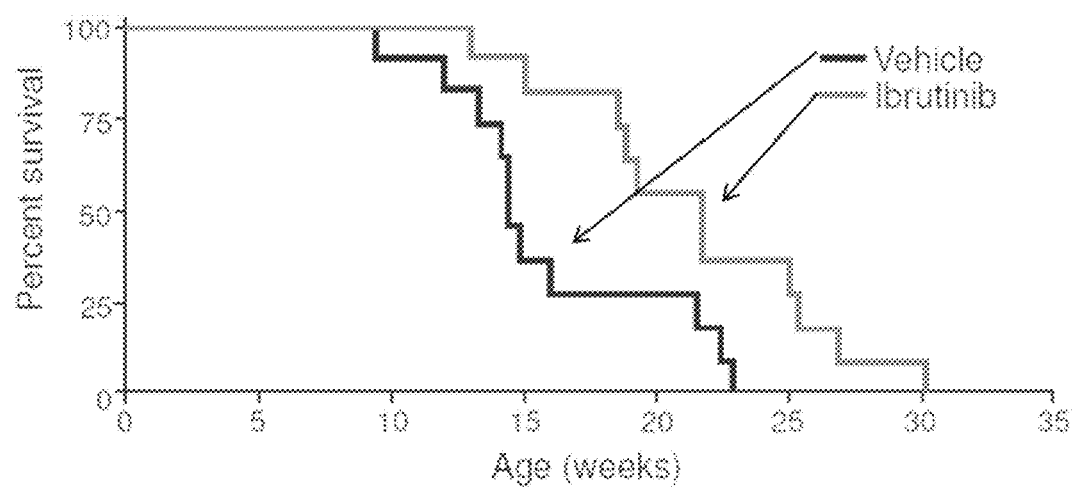
FIG. 3A and FIG. 3B illustrate the percentage of survival of mice in treatment with ibrutinib as a monotherapy or in combination with standard of care.
Figure 3B:
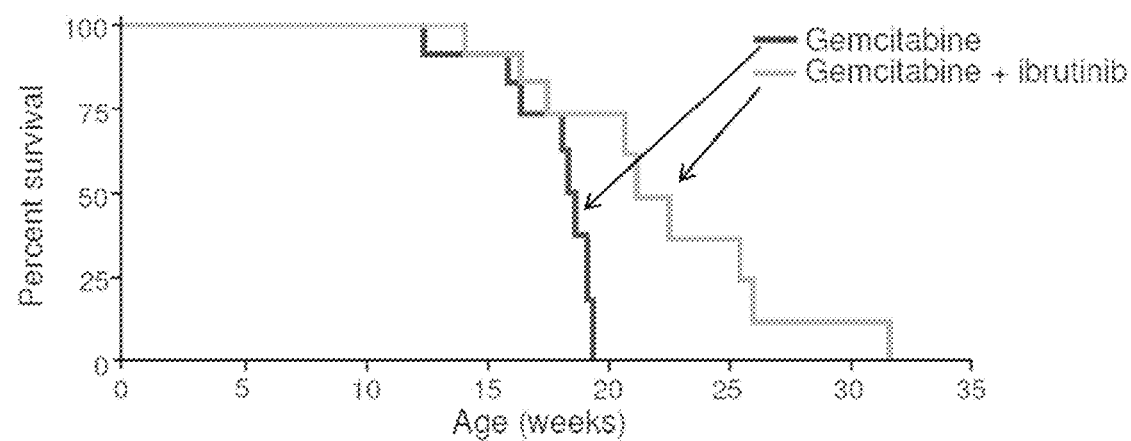

Ibrutinib was an Effective Therapy in PDAC and Improved the Outcome of Standard Care In PDAC, dense stromal fibrosis is a considerable obstacle to standard of care. Two independent survival experiments were undertaken to test the therapeutic impact of ibrutinib alone and to assess ibrutinib in combination with gemcitabine. As monotherapy, ibrutinib conferred a significant survival advantage to treated mice compared to untreated controls (FIG. 3A). In the ibrutinib+gemcitabine combined treatment, the survival advantage was also extended compared to gemcitabine alone (FIG. 3B), confirming that the standard of care outcome could be improved by the addition of ibrutinib.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

---

What is claimed is:

1. A method of treating pancreatic cancer in a pancreatic cancer patient having pancreatic fibrosis, comprising administering to the patient a therapeutically effective amount of a compound which is (R)-1-(3-(4-amino-3-(4-phenoxyphenyl)-1H-pyrazolo[3,4-d]pyrimidin-1-yl)piperidin-1-yl)prop-2-en-1-one (ibrutinib), of the structure:

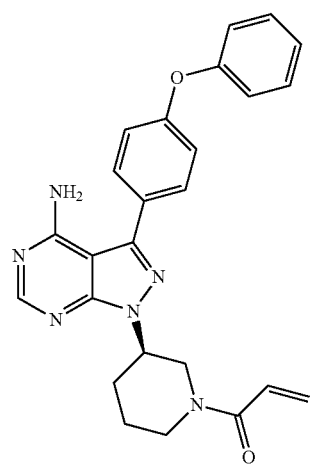 [SMILES: C=CC(=O)N1CCC[C@@H](n2nc(-c3ccc(Oc4ccccc4)cc3)c3c(N)ncnc32)C1]

2. The method of claim 1, wherein the pancreatic cancer is pancreatic ductal adenocarcinoma.

3. A method of treating pancreatic cancer in a pancreatic cancer patient having pancreatic fibrosis, comprising administering to the patient a therapeutically effective amount of a compound which is (R)-1-(3-(4-amino-3-(4-phenoxyphenyl)-1H-pyrazolo[3,4-d]pyrimidin-1-yl)piperidin-1-yl)prop-2-en-1-one (ibrutinib), of the structure:

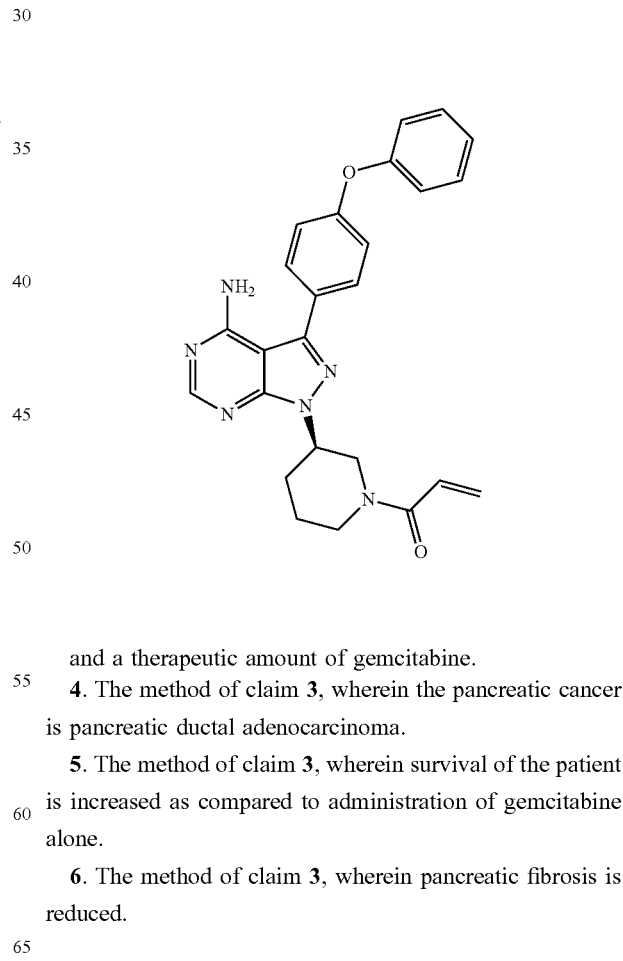

and a therapeutic amount of gemcitabine.

4. The method of claim 3, wherein the pancreatic cancer is pancreatic ductal adenocarcinoma.

5. The method of claim 3, wherein survival of the patient is increased as compared to administration of gemcitabine alone.

6. The method of claim 3, wherein pancreatic fibrosis is reduced.

* * * * *

UNITED STATES PATENT AND TRADEMARK OFFICE
CERTIFICATE OF CORRECTION

| | | |
|---|---|---|
| PATENT NO. | : 9,844,552 B2 | Page 1 of 1 |
| APPLICATION NO. | : 14/957294 | |
| DATED | : December 19, 2017 | |
| INVENTOR(S) | : Toni Jauset González et al. | |

It is certified that error appears in the above-identified patent and that said Letters Patent is hereby corrected as shown below:

On the Title Page

Item (12):
"Gonzá#lez et al."
Should read:
--González et al.--

Item (72) the first inventor's name:
"Toni Jauset Gonzá#lez"
Should read:
--Toni Jauset González--

Signed and Sealed this
Thirteenth Day of March, 2018

Andrei Iancu
*Director of the United States Patent and Trademark Office*